United States Patent
Chandok et al.

(10) Patent No.: US 8,450,053 B2
(45) Date of Patent: May 28, 2013

(54) ZAP-70 AS PREDICTOR AND MODULATOR OF EFFECTOR FUNCTION OF T CELLS

(75) Inventors: Meena Chandok, Odenton, MD (US); Donna Farber, Baltimore, MD (US); Francesca Okoye, Menlo Park, CA (US)

(73) Assignee: University of Maryland, Baltimore, Baltimore, MD (US)

( * ) Notice: Subject to any disclaimer, the term of this patent is extended or adjusted under 35 U.S.C. 154(b) by 204 days.

(21) Appl. No.: 12/733,636

(22) PCT Filed: Sep. 10, 2008

(86) PCT No.: PCT/US2008/010566
§ 371 (c)(1),
(2), (4) Date: Jun. 30, 2010

(87) PCT Pub. No.: WO2009/035600
PCT Pub. Date: Mar. 19, 2009

(65) Prior Publication Data
US 2010/0331391 A1    Dec. 30, 2010

Related U.S. Application Data

(60) Provisional application No. 60/971,441, filed on Sep. 11, 2007.

(51) Int. Cl.
*C12Q 1/00*    (2006.01)

(52) U.S. Cl.
USPC .............................................................. 435/4

(58) Field of Classification Search
None
See application file for complete search history.

(56) References Cited

U.S. PATENT DOCUMENTS
2003/0103938 A1* 6/2003 Jinquan et al. ............... 424/85.2

OTHER PUBLICATIONS

Okoye et al. Clinical Immunology 2007, vol. 125, pp. 5-15.*
Hall et al. European Journal of Immunology 1999, vol. 29, pp. 2098-2106.*

* cited by examiner

*Primary Examiner* — Tracy Vivlemore
(74) *Attorney, Agent, or Firm* — Pratt & Associates, Inc.; Sana A. Pratt

(57) ABSTRACT

In this application is described a novel, multiparameter analysis of TCR-coupled signaling and function in resting and activated naive and memory CD4 T cells, revealing a biochemical basis for immunological recall. Results reveal a novel biochemical signature imparted to memory CD4 T cells enabling efficacious responses through increased ZAP-70 expression and reduced accumulation of downstream signaling events.

3 Claims, 9 Drawing Sheets

ZAP-70 AS PREDICTOR AND MODULATOR OF EFFECTOR FUNCTION OF T CELLS

This is a U.S. National Phase application of PCT/US2008/010566, filed on Sep. 10, 2008 which claims priority under 35 U.S.C. 119(e) from U.S. Application Ser. No. 60/971,441 filed on Sep. 11, 2007, both of which are herein incorporated by reference in their entirety.

This invention was made with government support under NIH Grant No. A1042092 awarded by National Institutes of Health. The government has certain rights in the invention.

INTRODUCTION

Immune memory is characterized by efficacious responses to previously encountered antigens, mediated by memory T lymphocytes that produce effector cytokines immediately upon antigenic challenge. While the enhanced activation properties and potent functional capacities of memory CD4 and CD8 T cells are well-documented (Kaech et al., 2002, Nat. Rev. Immunol. 2, 251-262; Dubey et al., 1996, J. Immunol. 157, 3280-3289; Rogers et al., 2000, J. Immunol. 164, 2338-2346), the mechanisms by which T cell receptor (TCR) engagement is coupled intracellularly to rapid effector responses remain unknown. TCR-coupled intracellular signaling events have been extensively characterized in T cell lines and unfractionated primary T cells, revealing a progression of intracellular events linking TCR ligation to nuclear gene transcription (Kane et al., 2000. Curr. Opin. Immunol. 12, 242-249). Initial phosphorylation of the TCR-associated CD3ε and CD3ζ subunits by the proximal p56lck kinase results in the recruitment, phosphorylation and activation of the 70 kDa SH2-containing ZAP-70 tyrosine kinase (Chan et al., 1992, Cell 71, 649-662; Iwashima et al., 1994. Science 263, 1136-1139). ZAP-70 subsequently phosphorylates the linker-adapter molecules SLP-76 and LAT which serve as scaffolds for assembly of a signaling cluster triggering downstream MAP kinase activation, calcium flux, and IL-2 gene transcription (Jordan et al., 2003, Nat. Immunol. 4, 110-116). The participation of these TCR-coupled signaling intermediates in the distinct responses of naive versus memory T cells and in coupling to effector cytokine production remains undefined (Chandok and Farber, 2004, Semin. Immunol. 16, 285-294).

In this application, we show that the capacity of memory T cells to elicit rapid recall responses is mediated by alteration(s) in TCR-coupled signaling that are stably maintained in the resting state, and likely associated with acquisition of effector function during activation and differentiation of naive T cells. We had previously applied standard biochemical approaches to analyze TCR-coupled signaling in lysates derived from polyclonal naive and memory CD4 T cells isolated by cell surface phenotype, and had found decreased intracellular phosphorylation and coupling to linker adapter molecules in the memory subset (Farber et al., 1995, Immunity 2, 249-259; Farber et al., 1997, Eur. J. Immunol. 27, 2094-2101; Hussain et al., 2002, J. Immunol. 168, 1557-1565), although how these signaling changes coupled to rapid recall remained unknown. Thus, to investigate the signaling mechanisms for rapid recall, we took advantage of new reagents and multiparameter approaches for high resolution analysis of signal transduction molecules in the native state at the single cell level (Perez and Nolan, 2002, Nat. Biotechnol. 20, 155-162; Krutzik et al., 2005, J. Immunol. 175, 2357-2365). By applying a novel combination of single cell signaling analysis with intracellular cytokine staining, we examined signaling events in conjunction with cytokine production in antigen-specific and polyclonal naive and memory CD4 T cells in the resting state and following antigenic stimulation at different kinetic time points in vitro and in vivo.

We report here a striking and specific elevation in expression of the ZAP-70 protein tyrosine kinase in resting antigen-specific and polyclonal mouse memory compared to naive CD4 T cells, and distinct signaling pathways coupled to effector function in these subsets. High level ZAP-70 expression in memory CD4 T cells is stably maintained independent of protein synthesis, whereas low ZAP-70 expression in naive T cells increases with sustained (24-48 hrs) antigenic stimulation requiring new protein synthesis. We establish that ZAP-70 protein levels control effector function, as acquisition of effector function occurs only from activated T cells that have upregulated ZAP-70 expression to high levels, and conversely, specific downmodulation of ZAP-70 expression in memory CD4 T cells by siRNA-mediated knockdown or specific inhibitors reduces rapid effector function. Downstream of ZAP-70, we show quantitative differences in the accumulation of distal phosphorylation events associated with effector function in naive and memory subsets in vitro and in vivo.

We also analyzed ZAP-70 expression in human T cell subsets, and found that human peripheral blood CD45RO$^+$ memory CD4 T cells expressed the highest level of ZAP-70 protein that was twofold greater than ZAP-70 expression in CD45RA$^+$ phenotype adult CD4 T cells that contain heterogeneous population of naive and non-naive T cells (Song K, et al., 2005, Proc Natl Acad Sci USA 102:7916-7921) and threefold greater than pure naive CD4 T cells in cord blood. These results establish elevated ZAP-70 expression as a novel feature of antigen-specific and polyclonal mouse and human memory CD4 T cells. Furthermore, similar to the mouse system, short-term stimulation of human T cells also led to IFN-γ production exclusively from ZAP-70hi cells, validating our mouse results that hi-ZAP-70 is required for effector cytokine production.

Our findings reveal a biochemical basis for rapid recall by memory T cells, and also identify a new mechanism for control of TCR-coupled signaling and function via alterations in proximal kinase expression at the protein level.

SUMMARY OF THE INVENTION

The present inventors have demonstrated that the level of ZAP-70 protein directly controls T cell effector function. Effector function, as assessed by IFNγ production results exclusively from activated T cells that have up-regulated ZAP-70, and specific down-regulation of ZAP-70 expression in memory CD4 T cells with abrogated rapid effector functions.

Therefore, in this application is described a novel role for ZAP-70 as a predictor and a target for modulation of T cell effector function, including CD4 and CD8 T cells.

In one aspect, the present invention provides a functional biomarker for memory CD4 and CD8 T cells. The inventors have found that maintaining a high level of ZAP-70 protein is an inherent property of memory T cells. Therefore by measuring ZAP-70, functional memory T cells can be differentiated from non-functional memory T cells and resting naive T cells.

In another aspect, the present invention provides a method for assessing the capacity for effector cytokine production (including, for example, TNFα and IFNγ) in a cell without following detailed functional analysis.

In particular aspects the method comprises two rounds of screening. In one aspect, the first round of screening identifies whether ZAP-70 is increased and the second round of screening identifies a cytokine (including, for example, TNFα and IFNγ) correlated with increased ZAP-70.

In one aspect, the first round of screening comprises measurement of ZAP-70 levels in blood taken from a subject. The first round of screening comprises obtaining blood; surface staining blood cells for CD4 and/or CD8 along with surface markers specific for naive and memory CD4 and/or CD8 T cells (including, for example, CD44 and CD62L); and quantification of ZAP-70 in CD4 and/or CD8 T cells. The second round of screening comprises correlating a cytokine with increased ZAP-70 levels. The second round of screening comprises obtaining blood from a subject that has demonstrated increased ZAP-70 levels followed by purification of CD4 and/or CD8 T cells, activation of the same by, for example, an antigen, and measuring cytokine production (including, for example, TNFα and IFNγ) to determine cytokine correlates to the increased ZAP-70 levels. Cytokine correlates to increased ZAP-70 levels are important, for example, because any subsequent therapy can be tailored to increase or decrease TNFα and IFNγ depending on the type of disease and/or disease state. For example, if the increase in ZAP-70 level is minimum to moderate wherein TNFα is only produced and one needs to manipulate the system to produce IFNγ then one can manipulate the system to increase ZAP-70 levels to produce IFNγ. Likewise, for example, if increase in ZAP-70 level is very high and correlates with both TNFα and IFNγ production and one needs to avoid IFNγ production in the system then lowering the expression of ZAP-70 to a level to only produce TNFα would be required. The quantitative measurement of ZAP-70 and cytokine levels will also be helpful not only to guide the course of treatment, but also to predict the accurate onset/stage of disease. Where there is no cytokine correlate to increased ZAP-70, these findings can elucidate pathological conditions leading to only changes in ZAP-70 expression without any changes in a cytokine.

In certain aspects of the present invention, CD4 or CD8 T cells can be isolated from a subject from, for example, the spleen or from blood. In other aspects, CD4 or CD8 surface markers on cells can, for example, be stained for markers specific for memory CD4 or CD8 T cells, (including, for example, mouse memory T cells CD44hi, CD62Llo/CD62L heterogeneous, CD25lo; human memory T cells (CD45RO+, CD25lo)). Antibodies for these surface markers conjugated to different fluorochromes (FITC, PE, PERCP, APC, APC-cy7, PE-cy7) are available commercially. In other aspects, stained cells can, for example, be permeabilized and specific cytokines (including, for example, IFNγ and TNFα) detected by labeled antibodies (including, for example, antibodies of IFNγ and TNFα attached to different fluorochromes (e.g FITC, PE, APC, PE-cy7)). In other aspects, the stained and labeled cells are then analyzed by flow cytometry for ZAP-70 and a desired cytokine (including, for example, IFNγ and TNFα). These methods and others are described, for example, in the Materials and Methods and in the Examples. Other methods known in the art to clearly effectuate the objects and methods of the invention are also encompassed by the invention.

An advantage of the method described above over the measurement by other techniques, like ELISA and Elispot for detecting cytokines, is that using this method, one is able to know that specific cells (e.g., CD4 or CD8 T cells) having certain level of ZAP-70 protein are capable of secreting cytokines. In case of ELISA and Elispot, one can measure a cytokine level but one does not know the source of cells producing the cytokine.

In one aspect of the invention is provided a rapid method for assessing the capacity for effector cytokine production (TNFα and IFNγ) in a cell without following detailed functional analysis (as explained above).

In yet another aspect, the present invention provides a method for predicting and/or assessing the immune capacity of an individual. Changes in the immune capacity of an individual can act as an indication of onset/progression of different diseases and potential dysfunctions in disease states. For example the onset of a disease like rheumatoid arthritis, Type I diabetes, systemic lupus erythematosus (SLE), multiple sclerosis (MS), psoriasis or allograft rejection, may begin with changes in effector cytokine production (immune capacity). In other aspects, assessing the level of ZAP-70 in T cells (including, for example, CD4 and CD8 T cells) from an individual with an autoimmune disease may be predictive of active disease and/or may mark a particular autoreactive subset.

In another aspect, the present invention provides a method for designing effective vaccination strategies, and monitoring the effect of vaccination in an individual. Memory CD4 or CD8 T cells play an important role in developing effective vaccination against diseases. Our results demonstrate that good functional memory CD4 and CD8 T cells maintain a high level of ZAP-70 protein. Monitoring the level of T cells with increased levels of ZAP-70 for different durations can be a measure of whether or not an administered vaccine is effective in providing protection against infection with a disease antigen.

In still another aspect, the invention provides a method for designing vaccination strategies against diseases where effective vaccines have not yet been developed, such as, without limitation, cancer. The method includes enhancing an immune response to an agent which elicits a desired immune response in a subject, comprising administering to the subject an agent which increases production of ZAP-70, in an amount effective for said increase, and administering to the subject an agent which elicits a desired immune response.

In another aspect, the present invention provides a method for regulation of production of specific cytokines, namely TNF-α and IFN-γ, by manipulating ZAP-70 protein. Cytokines play a critical role in governing many important decisions such as the extent of pathology of different diseases, tumor regression, tumor progression, T cell division, inflammation, autoimmunity, etc. Manipulation of ZAP-70 can affect the outcome of disease and disease severity. An increase in ZAP-70 can be affected by contacting a CD4 or CD8 T cell with an agent, such as an agonist, such as an antigen/pathogen for which T cells were previously exposed, thereby producing an increase in ZAP-70 levels. A decrease in ZAP-70 can be affected by contacting a CD4 or CD8 T cell with an agent, such as an antagonist such as, for example and without limitation, picetannol and si-RNA of ZAP-70. Alternatively, by transformation of cells with over expression construct(s) specific for ZAP-70 to increase ZAP-70 or silencing construct to decrease ZAP-70. The nucleic acid sequence for ZAP-70 is publicly available (for example, mouse, NM_009539; human, NM_207519, NM_001079) and methods of designing vectors for overexpression or underexpression of the gene are known in the art. These constructs can be made using different vectors, like inducible, constitutive, viral vectors, etc. The chosen agent can be administered to a subject in an amount sufficient to produce the desired change in ZAP-70 in the subject.

In another aspect, the present invention provides a method for reducing immunopathology due to a response to challenge with a pathogen or allergen in a subject previously exposed to the pathogen or allergen or a variation thereof such that memory CD4 or CD8 T cells are activated, said method comprising administering to said subject an agent which inhibits ZAP-70 expression or function, thereby improving clinical outcome and reducing sickness or symptoms of disease. This is useful in reducing severity of allergies to specific antigens.

In yet another aspect, the invention provides a method to regulate T cell cytokine production by changing the level of ZAP-70 protein in a T cell. Our results establish a cause and effect relationship between quantity of ZAP-70 protein and cytokine production capacity. Once a threshold level of ZAP-70 for IFNγ production in different organisms like mouse or human is determined, the amount in T cells can be changed to reach the level desired for specific quantity of cytokine (including, for example, IFNγ) production.

In still another aspect of the invention is provided a method to regulate the amount of Th-1 cytokines as a whole. The cytokines IL-2, IFNγ, and TNF-α are known as Th-1 cytokines. Reduced levels of Th-1 cytokines alone can lead to the production of Th-2 cytokines. Such a change plays an important role in regulating the initiation and progression of many diseases such as diabetes, arthritis, cancer, and other autoimmune diseases. The method includes altering ZAP-70 levels in order to direct the immune system towards a desired effect.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION

Figure 1:
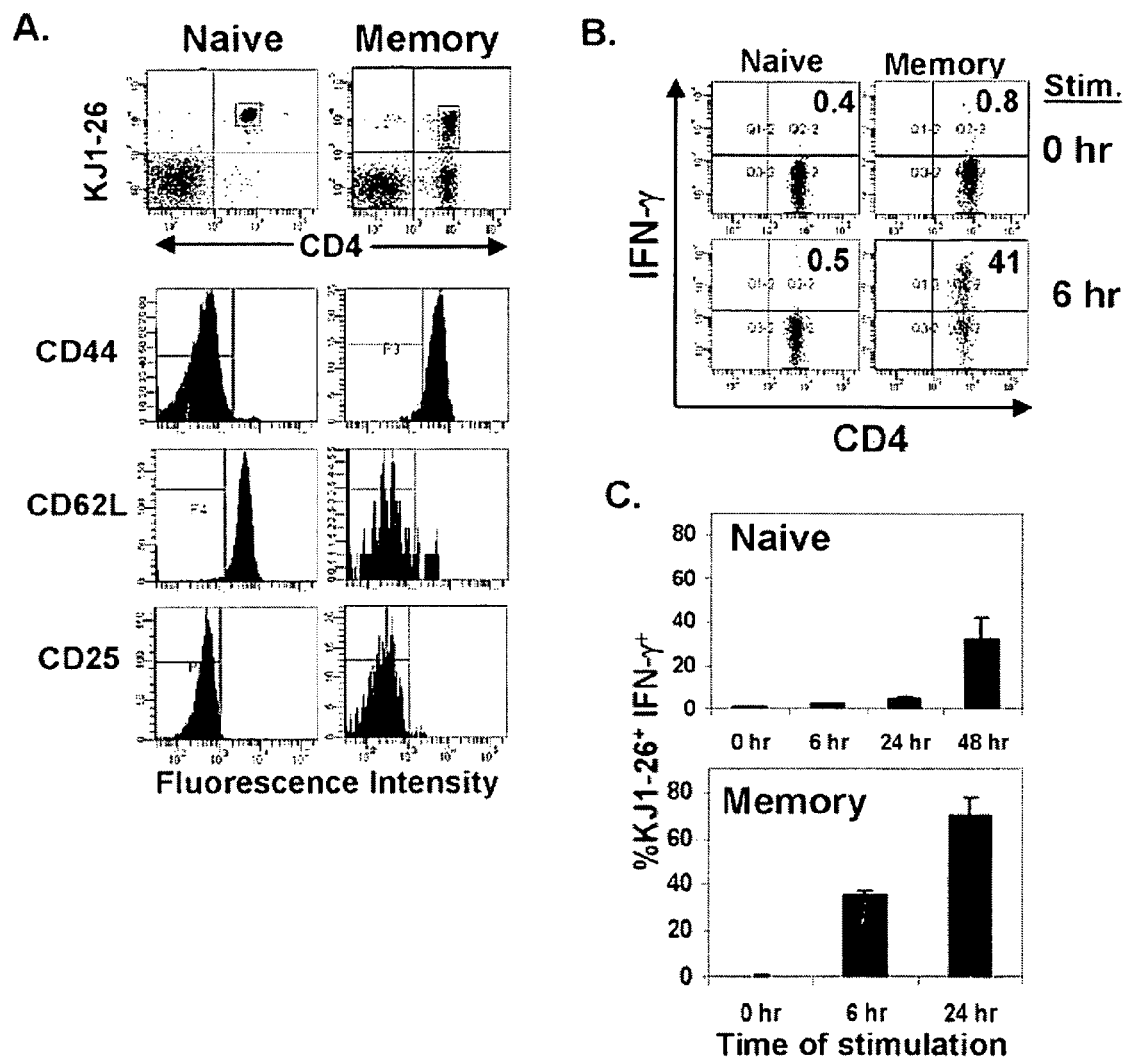
FIG. 1A, 1B, 1C. Phenotypic and functional comparison of OVA-specific naive and memory CD4 T cells. (A) Cell surface expression of CD44, CD62L and CD25 on resting OVA-specific naive CD4 T cells isolated from DO11.10XRAG2$^{-/-}$ mice and memory CD4 T cells isolated from RAG2$^{-/-}$ adoptive hosts >2 months post-transfer of primed DO11.10 effector CD4 T cells. Histograms are gated on KJ1-26$^+$CD4$^+$ T cells. Data are representative of >10 independent experiments. (B) IFN-γ production from resting and antigen-stimulated naive and memory CD4 T cells. OVA-specific naive and memory CD4 T cells were activated with OVA peptide and splenic APC for 6 hrs in the presence of monensin, and cytokine production was assessed by intracellular staining. Plots shown are gated on KJ1-26$^+$ cells, with quadrants drawn based on isotype controls. (C) Kinetics of IFN-γ production by antigen-stimulated naive and memory CD4 T cells. OVA-specific naive and memory CD4 T cells were activated as in (B) for 6-48 hrs and IFN-γ was assessed by ICS. The range in IFN-γ production from antigen-stimulated memory CD4 T cells was 20-40% at 6 hrs and 40-80% at 24 hrs in 15 different experiments.

In one aspect, the present invention provides a functional biomarker for memory CD4 and CD8 T cells. Since a high level of ZAP-70 is an inherent property of memory CD4 T cells, as compared to naïve T cells, the two cell types can be distinguished from each other and separated based on functional capacity of producing effector cytokines (including, for example, IFNγ, TNFα) if so desired. Methods for measuring ZAP-70 are shown in the Examples below and include without limitation, western blotting, flow cytometry, and real-time PCR. Samples used for measuring ZAP-70 and cytokines (including, for example, IFNγ, TNFα) include splenocytes and whole blood.

Design of immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide, ZAP-70, is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™ 1 or Immunlon™ 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are known in the art.

A monoclonal or polyclonal antibody which recognizes ZAP-70 can be used in an immunoassay for ZAP-70 (ZAP-70 antibodies can be obtained from, for example, BD-biosciences, Caltag (now with Invitrogen, Cell signaling technology), etc.). The antibodies involved in the invention can be labeled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. Such human monoclonal antibodies are prepared, for instance, by means of human peripheral blood lymphocytes (PBL) repopulation of severe combined immune deficiency (SCID) mice, or by means of transgenic mice in which human immunoglobulin genes have been used to replace the mouse genes.

Antibodies directed to peptides or portions of ZAP-70 or the whole protein may be used as a medicament, more particularly for incorporation into an immunoassay for the detection of ZAP-70 in a cell, for identification of the T cell type, or for therapeutic application as described below.

The present invention also relates to the use of any of the above-specified ZAP-70 monoclonal antibodies for the preparation of an immunoassay kit for detecting the presence of ZAP-70 protein or antigen in a biological sample, for the preparation of a kit for prognosis or diagnosis of a disease or for the preparation of a medicament.

The present invention also relates to a method for in vitro detection of ZAP-70 antigen present in a biological sample, spleenocytes or blood cells, comprising at least the following steps:

(ii) contacting said biological sample with a ZAP-70-specific monoclonal antibodies as defined above, under appropriate conditions which allow the formation of an immune complex, (iii) removing unbound components, (iv) incubating the immune complexes formed with heterologous antibodies, which specifically bind to the antibodies present in the sample to be analyzed, with said heterologous antibodies conjugated to a detectable label under appropriate conditions, (v) detecting the presence of said immune complexes visually or mechanically (e.g. by means of densitometry, fluorimetry, colorimetry).

The present invention also relates to a kit for in vitro detection or ZAP-70 present in a biological sample, comprising:

at least one monoclonal antibody as defined above, a buffer or components necessary for producing the buffer enabling binding reaction between these antibodies and the ZAP-70 antigens present in the biological sample, and a means for detecting the immune complexes formed in the preceding binding reaction.

The kit can possibly also include an automated scanning and interpretation device for inferring the amount of ZAP-70 present in the sample from the observed binding pattern.

By monitoring levels of ZAP-70 prior to vaccination and after vaccination at selected time points, e.g. 24 and 48 hours, 72 hours, etc. . . . , the effectiveness of the vaccine in mounting a protective immune response can be determined. For example, an increase in ZAP-70 in naïve T cells indicates an effective response towards the path of generating memory T cells whereas no increase in ZAP-70 indicates that naïve T cells could be defective and may not be able to give rise to functional effectors followed by generation of functional memory T cells against the vaccine antigen.

The present invention also relates to a method for in vitro detection of ZAP-70 and cytokines at the single cell level, in a biological sample comprising CD4 or CD8 T cells, comprising:

(i) contacting the biological sample with antibodies specific for surface antigens on CD4 or CD8 T cells;

(ii) contacting said biological sample with a ZAP-70-specific monoclonal antibodies as defined above, under appropriate conditions which allow the formation of a first immune complex, (iii) removing unbound components, (iv) contacting said biological sample with cytokine-specific antibodies (including, for example, IFNγ and TNFα), under appropriate conditions which allow the formation of a second immune complex;

(v) incubating the immune complexes formed with heterologous antibodies, which specifically bind to the antibodies present in the sample to be analyzed, with said heterologous antibodies conjugated to detectable labels which can be differentiated under appropriate conditions, (vi) detecting the presence of said immune complexes visually or mechanically (e.g. by means of densitometry, fluorimetry, colorimetry).

By identifying the first immune complex, comprising ZAP-70 antigen, and differentiating it from the second immune complex, comprising a cytokine (including, for example, IFNγ, TNFα), both ZAP-70 and cytokine production can be measured simultaneously by use, for example, of the respective antibodies conjugated directly to fluorochromes. Similarly, additional cytokines or antigens can be measured at the single cell level by providing antibodies with signaling molecules which can produce immune complexes which can be differentiated from the first and second immune complex. Additionally, transcripts of ZAP-70 present in the cells can be measured by using real-time polymerase chain reaction (PCR) assay well known in the art. Primers for use in detecting ZAP-70 can be designed by known methods using the publicly available sequence for ZAP-70.

Monoclonal antibodies according to the present invention are suitable both as therapeutic and prophylactic agents for treating or preventing diseases and conditions related to an elevation in ZAP-70 or for reducing ZAP-70 function or for regulating cytokine production (including, for example, IFNγ, TNFα) in a subject. Subjects include rodents such as mice or guinea pigs, monkeys, and other mammals, including humans.

In general, this will comprise administering a therapeutically or prophylactically effective amount of one or more monoclonal antibodies of the present invention to a subject in need of treatment. Any active form of the antibody can be administered, including Fab and $F(ab')_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before the desired effect can be reached, and the induced immune response to the MAbs in the subject does not induce "serum sickness" in the subject. Preferably, the MAbs administered exhibit some secondary functions such as binding to Fc receptors of the subject.

In another aspect of the invention is provided a method for altering levels of ZAP-70 in a cell in order to regulate effector function in a memory T cell in a subject. In specific aspects, the memory T cell is a naive T cell. In other specific aspects, the memory T cell is a CD4 or CD8 T cell. By regulating the level of ZAP-70, the level of specific cytokines, such as, for example, TNF-α and IFN-γ can be regulated. In the Examples below, using the mouse system, mean fluorescence intensity of ZAP-70 is used to provide relative levels of ZAP-70 in naïve T cells after activation with antigen. Changes in the relative value of mean fluorescence show that there is differential correlation to ZAP-70 for TNF-α and IFN-γ production (see, for example, Table 2). By altering the level of ZAP-70, one can modulate the CD4/CD8 T cells differentially to alter the levels of TNF-α and IFN-γ production. The levels can be increased or decreased depending on the type of desired cytokine production (including, for example, IFNγ, TNFα). A method for decreasing cytokine production comprises administering to the subject an agent that blocks or inhibits ZAP-70 protein production or function, in an amount effective in inhibiting said production or function, thereby downregulating or inhibiting ZAP-70 effector functions in memory T cells. Agents include piceatannol or antisense nucleotides.

Antisense oligonucleotides that are complimentary to a nucleic acid sequence from the ZAP-70 protein can also be used in the methods of the present invention to modulate the expression and/or activity ZAP-70.

Accordingly, the present invention provides a method of modulating the immune system by modulating the expression of ZAP-70. In one embodiment, the method of modulating the immune system by modulating the expression of ZAP-70 comprises administering an effective amount of an antisense oligonucleotide that is complimentary to a nucleic acid sequence from ZAP-70 to an animal in need thereof.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo. In one embodiment, the antisense oligonucleotide may be delivered to cells in a liposome formulation.

In a method for increasing cytokine (including, for example, IFNγ and TNFα) production, an agent can be administered which increases ZAP-70 protein production in naïve and memory T cells (including, for example, CD4 and CD8 T cells) in a subject, in an amount effective for increasing said ZAP-70 production, thereby upregulating or enhancing ZAP-70 effector functions to enhance said cytokine production, in said naïve and memory T cells.

For example, without limitation, an increase in ZAP-70 expression or function may be desired when a vaccine is administered in order to increase the immunity of the vaccine. On the other hand, a decrease in ZAP-70 function or expression may be desired to reduce immunopathology due to an inappropriate immune response due to disease conditions including inflammation, autoimmunity, or allergies. The decrease can be affected by contacting a CD4 T cell with an agent, in an amount sufficient to inhibit expression or function of ZAP-70 in the cell, in a subject.

In addition, the invention provides a method for downregulating or inhibiting an immune response driven by memory CD4 or CD8 T cells in a subject, comprising administering to the subject an agent that blocks or inhibits ZAP-70 function as described above, in an amount effective for inhibiting the effector cytokine expression, thereby reducing or inhibiting said immune response.

Also provided is a method for reducing immunopathology in response to challenge with a virus in a subject previously exposed to said virus comprising administering to said subject an agent which inhibits ZAP-70.

The present invention further provides a method of treating or preventing an autoimmune disease driven by effector-memory T cells, comprising administering to the subject an effective amount of an agent that blocks or inhibits ZAP-70, such that effector cytokine (including, for example, IFNγ and TNFα) production is altered or reduced, and/or immune response is reduced and autoimmune symptoms are reduced.

The present invention further provides a method of treating or reducing allograft rejection driven by memory T cells, comprising administering to the subject an effective amount of an agent that blocks or inhibits ZAP-70, such that cytokine production (including, for example, IFNγ and TNFα) is altered in type or amount, and/or said immune response is reduced.

Other reagents can be coupled or linked to the antibody or ligand of this invention for a specific purpose, e.g. ease in detection and tracking or for treatment at the target site. Multiple molecules of a reagent can be coupled to one antibody or ligand molecule, or more than one type of reagent can be coupled to one antibody or ligand. Alternatively, a carrier can also be used.

Suitable reagents include, but are not limited to, radionuclides, drugs, toxins, and derivatives thereof. Examples of radionuclides include, but are not limited to $^{90}Y$, $^{123}I$, $^{125}I$, $^{131}I$, $^{186}Re$, $^{188}Re$. Examples of drugs include methotrexate, and pyrimidine and purine analogs. Examples of toxins include lectins (e.g. ricin), diphteria toxin, cholera toxin, Pseudomonas exotoxin, Shigella toxin, and pokeweed antiviral protein.

Immunopathology is defined as deleterious side-effects of an immune response such as weight loss, inflammation, anatomical pathology, including extensive cellular inflammation and recruitment to a tissue site, and lengthened duration of sickness.

By previously exposed is meant exposed, through illness, infection or vaccination to the antigen, or molecule inducing an immune response or the virus or a form of the virus.

Cytotoxic drugs that interfere with critical cellular processes including DNA, RNA, and protein synthesis, can also be conjugated to antibodies and ligands and used for in vivo therapy.

As used herein, memory CD4 and CD8 T cells include a subset of cells, which arise from naïve CD4 and CD8 T cells. Upon exposure to cognate antigen, a subset of the antigen-experienced CD4 or CD8 T cells proliferate and differentiate to become long-lived resting memory T cells. Memory T cells exhibit enhanced activation properties relative to naive T cell counterparts and produce potent effector cytokines (including, for example, TNFα and IFNγ) rapidly and have reduced requirement of quantity of antigen present and costimulation for activation and have phenotypic properties mentioned above. Memory CD4 and CD8 T cells include cells defined by the upregulated levels of the adhesion marker CD44hi, and in humans are CD45RO+. Memory CD4 and CD8 T cells can also be subdivided into effector-memory T cells that lack of CD62L and/or CCR7 expression, expressing a CD62Llo/CCR7-phenotype, and central-memory T cells which bear a $CD26L^+/CCr7^+$ phenotype. CD3 association with ZAP-70 indicates the association of ZAP-70 with the TCR complex which may be important in regulating effector cytokines (including, for example, IFNγ and TNFα) production in a system.

In the methods of the invention, in addition to the administration to a subject of an agent that blocks ZAP-70 production or function, a reagent is also administered to the subject that targets an infectious agent and/or elicits an immune response in the subject. Thus, in certain embodiments, altering ZAP-70 expression by administration of the first agent, allows for the second reagent to impart an enhanced activity in the subject in the treatment of an infection, in enhancing an immune response to a vaccine, or in treatment of symptoms of a disease.

The second reagent can be administered in any vehicle form that allows the reagent to impart a therapeutic effect. A variety of immunization vehicles are known in the art, including, but not limited to, proteins and peptides, viral vectors, recombinant virus particles, vaccine (live, attenuated, killed, subunit, recombinant, protein, nucleic acid, etc.), nucleic acid (RNA or DNA), expression cassettes, plasmids, particles, liposomes, and other carriers, etc. The selection, production, evaluation and administration protocols of such vehicles and systems are known in the art. The second reagent can also be a drug, a small molecule, or other therapeutic compound or agent that acts to treat an infection in the subject.

The second reagent can also be a cancer antigen, i.e. an antigen specifically associated with cancer cells, for example BRCA1 antigen for breast cancer, and others known in the art. A cancer antigen can also be an antigen specific for a tumor present in a particular subject (e.g. an autologous tumor antigen). The present invention also contemplates the use of allergic antigens or allergens, which can include, but are not limited to, environmental allergens such as dust mite allergens, plant allergens such as pollen, insect allergens such as been venom and ant venom, and animal allergens such as cat dander and dog dander, and animal saliva allergens.

In many embodiments, the methods of the invention are directed to humans, but subjects can also include, for example, animals such as dogs, cats, horses, and other domestic and commercially important animals.

A subject of this invention can also include any animal in which an autoimmune disease such as rheumatoid arthritis, Type I diabetes, systemic lupus erythematosus (SLE), multiple sclerosis (MS), psoriasis or allograft rejection is to be treated and/or prevented. In addition, a subject can be an animal or human wherein protection from immunopathology due to infection or reinfection with a pathogen is desired.

In the methods of this invention, wherein an infection is treated, the infection can be caused by any pathogenic agent. Some examples include, but are not limited to, viral pathogens (e.g. influenza, hepatitis type A, hepatitis type B, hepatitis type C, influenza (all serotypes), varicella, adenovirus, herpesvirus, rhinovirus, echovirus, rotavirus, lentivirus, retrovirus, respiratory syncytial virus, papilloma virus, papova virus, cytomegalovirus, coronavirus, arbovirus, hantavirus, coxsckie virus, mumps virus, measles virus, rubella virus, polio virus, human immunodeficiency virus type I (HIV-1), and human immunodeficiency virus type II (HIV-II); prokaryotic pathogens (e.g. mycobacteria, *rickettsia*, *Mycoplasma* spp., *Neisseria* spp. and *Legionella* spp., *chlamydia*); and protozoal pathogens (e.g. *Leishmania* spp. and *Trypanosoma* spp.).

In the methods of this invention, the agent that blocks ZAP-70 expression in a subject can be administered prior to infection, or anytime following infection to the subject once, more than once, at any interval, so that a specific amount of the agent is maintained in the subject for a period of time, or the agent is administered such that it is present in the subject only transiently. In one embodiment, at least zero, one, two, three, four, five, six, seven, eight, nine or ten days before a reagent that acts to elicit an immune response is administered to the subject.

Pharmaceutical compositions comprising the agent of this invention and a pharmaceutically acceptable carrier are also provided. The compositions described herein can be formulated for administration in a pharmaceutical carrier in accordance with known techniques. See, e.g., Remington, The Science And Practice of Pharmacy (latest edition). By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation.

The pharmaceutical compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, Pharmaceutical Research 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

An effective amount of a composition of this invention, the use of which is in the scope of present invention, will vary from composition to composition, and subject to subject, and will depend upon a variety of well known factors such as the age, race, gender and condition of the subject and the form of the composition and route of delivery. An effective amount can be determined in accordance with routine pharmacological procedures known to those skilled in the art (see, e.g., Remington's Pharmaceutical Sciences, latest edition).

The compositions of this invention can be administered to a cell of a subject either in vivo or can be administered ex vivo in autologous cells treated ex vivo and readministered in vivo via adoptive cellular therapy. For administration to a cell of the subject in vivo, as well as for administration to the subject, the compositions of this invention can be administered, for example as noted above, orally, parenterally (e.g., intravenously), by intramuscular injection, intradermally (e.g., by gene gun), by intraperitoneal injection, subcutaneous injection, transdermally, extracorporeally, topically or the like. Also, the composition of this invention may be pulsed onto specific cells such as peripheral blood T lymphocytes which are isolated or grown from patient cells, according to methods well known in the art, or onto bulk PBMC or various cell subfractions thereof from a patient.

If ex vivo methods are employed, cells or tissues can be removed and maintained outside the body according to standard protocols well known in the art while the compositions of this invention are introduced into the cells or tissues. The transduced cells can then be infused (e.g., in a pharmaceutically acceptable carrier) or transplanted back into the subject per standard methods for the cell or tissue type. Standard methods are known for transplantation or infusion of various cells into a subject. Thus, in one embodiment of this invention, the agent of this invention can be presented to the immune system in a subject on the surface of a cell (i.e., as a cell surface antigen present in the plasma membrane of the cell) and in other embodiments can be presented to the immune system in a subject as a non-cell associated (i.e., cell-free) agent.

"Effective amount" refers to an amount of an agent or composition of this invention that is sufficient to produce a desired effect, which can be a therapeutic effect. The effective amount will vary with the age, gender, race, species, general condition, etc., of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, The Science And Practice of Pharmacy (20th ed. 2000)).

"Treat," "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay in the progression of the condition, prevention or delay of the onset of the disorder, and/or change in clinical parameters, disease or illness, etc., as would be well known in the art.

A "subject in need thereof" is a subject known to be, or suspected of having an autoimmune disease or allograft rejection or of having an infection or other pathological condition as described herein. A subject of this invention can also include a subject not previously known or suspected to have autoimmune disease or an infection or in need of treatment for a disease or infection. For example, a subject of this invention can be administered the compositions of this invention-even if it is not known or suspected that the subject has cancer or an infection (e.g., prophylactically). A subject of this invention is also a subject known or believed to be at risk of an autoimmune disease, or allograft rejection or infection.

It is also contemplated that the compositions of this invention can be used as a vaccine or prophylactic composition and employed in methods of preventing a disease or disorder in a subject, comprising administering to the subject an effective amount of the composition of this invention. The vaccine can be administered to a subject who is identified to be at risk of contracting a particular disease or developing a particular disorder and in whom the ability to elicit an immune response to an antigen may be impaired. Identification of a subject at risk can include, for example, evaluation of such factors as family history, genetic predisposition, age, environmental exposure, occupation, lifestyle and the like, as are well known in the art.

The present invention additionally provides kits comprising a first agent for reducing or blocking ZAP-70 expression in a subject and a second reagent for treating and/or preventing cancer and/or an infectious disease or disorder in a subject, with or without an adjuvant, along with appropriate buffers, diluents, vessels and/or devices, etc. for measuring a specific amount and for administering the compositions to a subject of this invention.

All publications, including, but not limited to patents and patent applications, cited in this specification are herein incorporated by reference as if each individual publication were specifically and individually indicated to be incorporated by reference herein as though fully set forth.

The invention is further described in detail to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided therein.

EXPERIMENTAL PROCEDURES

Mice

BALB/c mice (8-16 weeks of age) were obtained from the National Cancer Institute Biological Testing Branch. DO11.10XRAG2$^{-/-}$ mice (Taconic Farms, Germantown, N.Y.), DO11.10 mice (Murphy et al., 1990, Science 250, 1720-1723) bred as heterozygotes onto BALB/c backgrounds, and RAG2$^{-/-}$ mice (Shinkai et al., 1992, Cell 68, 855-867) on BALB/c backgrounds (Taconic Farms) were maintained in the Animal Facility at the University of Maryland Medical Center (Baltimore, Md.) under specific pathogen-free conditions.

Reagents

The following antibodies were purified from bulk culture supernatants and purchased from BioExpress (West Lebanon, N.H.): anti-CD8 (TIB 105), anti-CD4 (GK1.5), anti-1-A$^d$ (212.A1), and anti-Thy-1 (TIB 238). Different fluorochrome conjugated antibodies used in this study were purchased from BD Pharmingen (San Diego, Calif.), CALTAG Laboratories (Burlingame, Calif.), eBioscience (San Diego, Calif.), Sigma (St. Louis, Mo.) and Cell Signaling Technologies (Danvers, Mass.). Clone and fluorochrome details of all antibodies used in this study are provided in Table 1. OVA peptide (323-339, ISQAVHAAHAEINEAGR SEQ ID NO:1) was synthesized by the Biopolymer Laboratory at the University of Maryland School Of Medicine.

Generation of Effector and Memory CD4 T Cells

OVA-specific naive CD4 T cells were isolated from spleens of DO11.10XRAG2$^{-/-}$ mice by immunomagnetic depletion (Patke and Farber, 2005, J. Immunol. 177, 5433-5443), or by direct sorting of Thy1$^+$ T cells using anti-CD90-conjugated magnetic beads (Miltenyi, Auburn, Calif.) and the autoMACS™ for analysis by real-time PCR, western blotting and by confocal microscopy. Generation of OVA-specific memory CD4 T cells in vivo was accomplished using an adoptive transfer system extensively validated in the laboratory (Bingaman et al., 2005, Eur. J. Immunol. 35, 3173-3186; Moulton et al., 2006, J. Immunol. 177, 869-876; Patke and Farber, 2005, supra; Ahamdzadeh and Farber, 2002, Proc. Natl. Acad. Sci. USA 99, 11802-11807). Briefly, in vitro primed (for 48 hrs unless specified otherwise) DO11.10 effector cells were transferred into RAG2$^{-/-}$ adoptive hosts (5×10$^6$/mouse) and persisting memory CD4 T cells were harvested from spleen after 2-5 months post-transfer for subsequent analysis (see below).

Western Blotting

For western blot analyses, T cells (2×10$^6$) were lysed in SDS sample buffer with protease/phosphatase inhibitors and were probed with primary (CD3, ZAP-70) and HRP-conjugated secondary antibodies as described (Iwashima et al., 1994, supra; Patke et al., 2005, Clin. Immunol. 117, 125-132). Blots were scanned using a Flatbed Canon Scanner (LiDE60) and densitometric analysis of the autoradiograms was performed with 1Dscan Ex3.1 Evaluation system (Scanalytics, Inc, Fairfax, Va.).

TABLE 1

Clone and fluorochrome details of antibodies used in this study.

| Antibody | Clone | FITC | PE | PERCP | APC | APC-CY7 | PE-CY7 |
|---|---|---|---|---|---|---|---|
| Phosphotyrosine | PT-66 | * | | | | | |
| ZAP-70 | 1E7.2 | * | * | * | | | |
| Phospho-ZAP-70 (Y319) | 17-P/ZAP-70 | | | * | | | |
| Phospho-PLC | 27/PLC | * | | * | | | |
| Phospho-P42 | E10 | * | | | | | |
| Phospho-P38 | 28B10 | * | | | | | |
| Phospho-Stat1 | 4a | * | | | | | |
| CD3ε chain | 145-2C11 | * | * | | | | |
| CD25 | PC61 | | * | | | * | |
| CD69 | H1.2F3 | * | * | | | | |
| CD4 | GK1.5 | | | * | | * | * |
| CD62L | MEL-14 | * | | | | | * |
| CD45RB | 16A | | * | | | | |
| CD44 | IM7 | * | | | | | |
| IFN-γ | XMG1.2 | * | * | | | * | |
| DO11.10 TCR | KJ1-26 | | * | | * | | |
| CD45RO | UCHL1 | * | * | | | | |
| CD45RA | H100 | * | * | | | | |

Quantitative Real-Time PCR

Primers for detection of CD4, ZAP-70, GAPDH and hypoxanthine phosphoribosyltransferase (HPRT) mRNAs were designed using the Primer Express 2.0 program (Applied Biosystems). Total cDNA was isolated from CD90-sorted naive and memory CD4 T cells using cDNA synthesis kit from NEB. Total cDNA (30 ng) was used as starting material for real-time PCR quantitation with SYBR® Green (Applied Biosystems, Foster City, Calif.) on an Applied Biosystems 7900HT. Ct values were compared using the delta-delta-Ct method using HPRT and GAPDH as a housekeeping gene (Livak and Schmittgen, 2001, Methods, 25, 401-408). (GAPDH Primers, 5'→3' forward SEQ ID NO:2 agc ctc gtc ccg tag aca aaa t and reverse SEQ ID NO:3 tgg caa caa tct cca ctt tgc) (HPRT Primers, 5'→3' forward SEQ ID NO:4 get gac ctg ctg gat tac att aa and reverse SEQ ID NO:5 tga tca tta cag tag ctc ttc agt ctg a) (ZAP-70 Primers, 5'→3' REVERSE SEQ ID NO: 6 gta aat tag tcc atc cgc ctt ca and 5'→3' Forward SEQ ID NO:7 ctc tgg cag ctg gtg gag tac) (CD4: 5'→3' Primers, forward SEQ ID NO: 8 act ggt tcg gca tga cac tct and 5'→3' reverse SEQ ID NO:9 tga tag ctg tgc tct gaa aac cc). Conditions of reaction: Stage 1 50 C, 2 min; Stage 2: 95 C, 10 min; Stage 3: 95 C, 15 sec, 60 C, 1 min (40 cycles), Stage 4: 95 C, 15 sec, 60 C, 15 sec, 95 C, 15 sec.

Intracellular Cytokine Staining

Intracellular cytokine staining (ICS) analysis of signaling intermediates and cytokines was performed as previously described (Bingaman et al., 2005, supra; Ahmadzadeh and Farber, 2002, supra). Briefly, naive or memory CD4 T cells were cultured with APC and 800 ng/ml OVA peptide for time points of 0-48 hrs, and monensin (Golgistop™, BD Pharmingen) was added 6 hrs prior to harvesting. Cells were stained with antibodies for surface markers CD4, CD25, CD44, KJ1-26, fixed (Cytofix™ buffer, BD Pharmingen), permeabilized, and stained intracellularly with fluorochrome-conjugated antibodies to cytokines, signaling intermediates, and analyzed by flow cytometry.

In Vivo Stimulation of Naive and Memory CD4 T Cells

Mice were administered 6 ug anti-CD3 antibody (C363.29B) or murine IgG2a as described (Scott et al., 1990, J. Immunol. 145, 2183-2188). Spleens were removed after 4 hrs and splenocytes incubated in complete Clicks medium in the presence of monensin (Golgistop™, BD Pharmingen) for an additional 2 hrs, followed by surface and intracellular staining, and were analyzed by flow cytometry.

Flow Cytometry

Six-color flow cytometry was performed on BD LSR II flow cytometer (BD Biosciences) using FITC, PE, PERCP and PE-Cy7, allophycocyanin-Cy7, and allophycocyanin as fluorochromes (BD Biosciences, e-biosciences, Invitrogen/caltag). CD4 T cells stained with single color fluorochromes were used for compensation, background values were established with isotype controls, and data were analyzed using BD FACSDiva™ software (BD Biosciences). Fluorochrome-conjugated antibodies directed against CD4 (clone GK1.5), CD25 (PC61), CD69 (H1.2F3), CD62L (MEL-14), CD44 (IM7), CD3ε (145-2C11), IFN-γ (XMG1.2), phospho-ZAP-70 (17-P), phospho-PLC-γ (27/PLC), and phospho-Stat1 (clone 4a) were all purchased from BD-Pharmingen (San Diego, Calif.). PE- and APC-conjugated KJ1-26 specific for the DO11.10 TCR clonotype were purchased from CALTAG Laboratories (Burlingame, Calif.). PE- and FITC-conjugated ZAP-70 (1E7.2) was obtained from Invitrogen (Carlsbad, Calif.), and FITC-conjugated phospho-tyrosine (PT-66) from Sigma (St. Louis, Mo.), and phospho-p38 (28B10) and phospho-erk1/2 (E10) were purchased from Cell signaling technology, Inc. (Danvers, Mass.). For most analyses, a given marker was analyzed using several different fluorochromes to eliminate errors based on compensation.

Human CD4 T Cell Isolation and Functional Analysis

Heparinized peripheral venous was obtained from consenting healthy adult volunteers, and cord blood obtained from full term placentae. CD4 T cells were purified by negative selection using the CD4 T cell isolation kit and autoMACS™ (Miltenyi Biotec), and subsequently depleted of CD4+ CD25+ T cells using anti-CD25 conjugated microbeads (Miltenyi Biotec), yielding >98% pure CD4+CD25− T cells. For intracellular cytokine staining, T cells were stimulated with Dynabeads® CD3/CD28 for 6 h in the presence of Golgistop (BD Pharmingen), before staining and analysis.

Confocal Microscopy

Naive and memory CD4 T cells were purified by sorting with anti-CD90 beads (Miltenyi) and were adhered to slides. Cells were surface stained for CD3ε, then permeabilized and stained for ZAP-70 or isotype controls. Cells were analyzed with a confocal microscope (Zeiss LSM510 META Confocal Microscope).

Inhibitor Assays

Naive or memory CD4 T cells ($1\times10^6$) were cultured with APC ($3\times10^6$) in total volume of 1 ml of Clicks medium containing 800 ng/ml OVA peptide for time points of 0-24 hrs along with inhibitors cycloheximide (Sigma, 50 μg/ml) or piceatannol (Calbiochem, 12 μM of 3,4,3',5'-tetrahydroxy-trans-stilbene). Solvent alone served as a vehicle control.

siRNA-Mediated Knockdown

Cy3-labeled ZAP-70 specific siRNA Sense (5'→3')/Cy3/GGCGGAUGGACUAAUUUACtt (SEQ ID NO: 10); Antisense (5'→3') GUAAAUUAGUCCAUCCGCCtt (SEQ ID NO:11) or control GAPDH siRNA obtained from Ambion (Austin, Tex.) was delivered at a final concentration of 5 μM into $1.0\times10^6$ purified resting memory OVA-specific CD4 T cells using the mouse T cell nucleofector kit (Amaxa Inc., Gaithersburg, Md.) according to the manufacturers instructions and similar to the approach previously employed for siRNA transfections in mouse T cells (Sabbagh et al., 2006, Proc. Natl. Acad. Sci. USA 103:18703-18708). Following nucleofection, cell suspensions were cultured in media in 24 well plates with APC ($2\times10^6$/well) and OVA-peptide (800 ng/ml), followed by incubation at 37° C. for 18 hrs. After 18 hrs, Golgistop (BD Pharmingen, USA) (0.66 μl/ml of culture) was added, cells were incubated for an additional 6 hrs, and subsequently staining for surface expression of CD4, KJ1-26 and CD25, and intracellular expression of ZAP-70 and IFN-γ as above.

Example 1

Phenotype and Function of Antigen-Specific Naive and Memory CD4 T Cells

For investigating the functional coupling of signaling pathways in antigen-specific naive and memory CD4 T cells, we used DO11.10 TCR transgenic CD4 T cells expressing the KJ1-26 TCR clonotype specific for an ovalbumin peptide (OVA). Naive, OVA-specific CD4 T cells were obtained from DO11.10XRAG2$^{-/-}$ mice, exclusively expressing KJ1-26$^+$ CD4 T cells bearing a CD25lo/CD44lo/CD62Lhi naive phenotype (FIG. 1A). OVA-specific memory CD4 T cells were generated by in vitro priming of CD4 T cells obtained from DO11.10 mice on a BALB/c background with OVA peptide and splenic APC (OVA/APC) followed by in vivo adoptive transfer into RAG2$^{-/-}$ hosts based on a system extensively validated in the laboratory (Bingaman et al., 2005, Eur. J. Immunol. 35, 3173-3186; Moulton et al., 2006, J. Immunol. 177, 869-876; Ahmadzadeh and Farber, 2002, supra; Ahmadzadeh et al. 2001, J. Immunol. 166, 926-935; Ndejembi et al., 2006, J. Immunol. 177, 7698-7706; Patke et al. 2005, Clin. Immunol. 117, 125-132). The resultant memory T cells exhibit the phenotype, function and activation properties of memory CD4 T cells similarly generated in intact BALB/c hosts or by in vivo priming (Bingaman et al., 2005, supra; Moulton et al., 2006, supra; Ahamdzadeh and Farber 2002, supra; Ndejembi et al., 2006, supra). The KJ1-26$^+$ OVA-specific memory CD4 T cells generated here are CD25lo, CD44hi and predominantly CD62Llo (FIG. 1A). (KJ1-26$^-$ CD4 T cells in memory hosts derive from carryover and expansion of transferred T cells with endogenous receptors). Functionally, they exhibit rapid production of IFN-γ following 6 hrs of antigenic stimulation (FIG. 1B, right), whereas naive CD4 T cells do not produce IFN-γ at this early time point (left). Kinetic analysis of IFN-γ production from OVA-specific naive and memory CD4 T cells, shows that naive DO11.10 CD4 T cells require 48 hrs of sustained antigen activation to produce IFN-γ similar to memory CD4 T cells activated with antigen for only 6 hrs, with nearly all memory CD4 T cells exhibiting effector function (80%) at 24 hrs post-antigen recall (FIG. 1C). After 48 hrs of antigen stimulation, there is substantial attrition of memory T cells (Patke and Farber, 2005, supra), and this time point is not included in this study.

Example 2

Expression of Signaling Intermediates in Resting Naive and Memory CD4 T Cells

Figure 2:
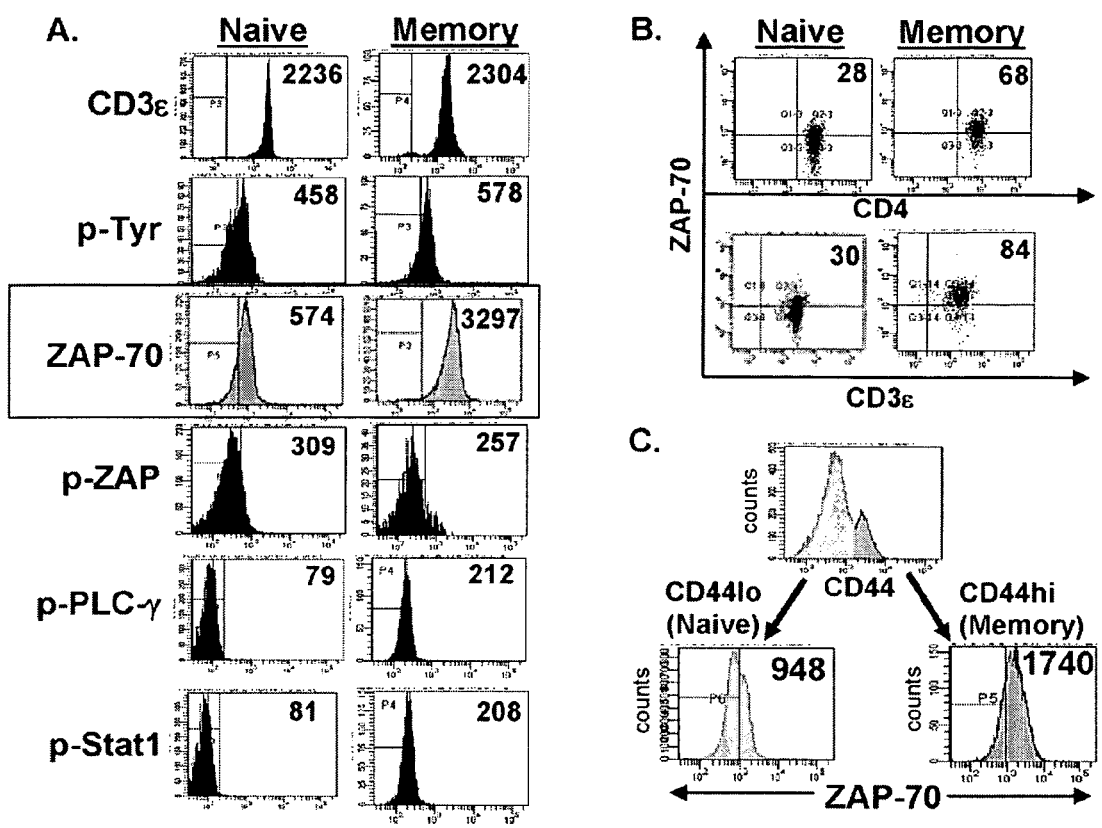
FIG. 2A, 2B, 2C. Expression of intracellular signaling molecules in resting naive and memory CD4 T cells. (A) OVA-specific naive and memory CD4 T cells isolated as in FIG. 1 were stained intracellularly for CD3ε, total tyrosine phosphorylation (p-Tyr), ZAP-70 protein, phosphorylated ZAP-70 (p-ZAP), phosphorylated PLC-γ (p-PLC-γ) and phosphorylated Stat1 (p-Stat1). Histograms shown are gated on CD4$^+$KJ1-26$^+$ cells, with markers drawn based on isotype controls, and mean fluorescence intensity (MFI) values are shown as inset. (B) Co-expression of ZAP-70 and CD4 (upper panels) or ZAP-70 and CD3ε (lower panels) in resting naive and memory CD4 T cells gated on CD4$^+$KJ1-26$^+$ cells, with markers drawn based on isotype controls. Numbers in quadrants represent the percentage of ZAP-70hiCD4$^+$ or ZAP-70hiCD3ε$^+$. (C) Expression of ZAP-70 in polyclonal naive (CD44lo) and memory (CD44hi) CD4 T cells. Results show CD44 expression of polyclonal CD4 T cells from BALB/c mice, with ZAP-70 histograms gated on CD4$^+$CD44lo (naive) and CD4$^+$CD44hi (memory) populations. Numbers in histograms indicate mean fluorescence intensity. Data are representative of three independent experiments.

We performed an extensive analysis of the expression and phosphorylation state of signaling intermediates in resting OVA-specific naive and memory CD4 T cells using multiparameter flow cytometry (see methods) to test our hypothesis that qualitative and/or quantitative alterations in TCR-mediated signaling in memory versus naive CD4 T cells may account for their distinct effector capacities. Representative results show expression of each signaling intermediate as histograms gated on the CD4$^+$KJ1-26$^+$ population (see FIG. 1A) and quantified based on mean fluorescence intensity (FIG. 2A). In general, most of the signaling parameters examined (see Table I) did not differ significantly in resting naive and memory CD4 T cells, including expression of the TCR-coupled signaling subunit CD3ε (FIG. 2A, row 1), total intracellular tyrosine intracellular (p-Tyr; row 2), and lack of basal phosphorylation on tyrosine 319 (Di Bartolo et al., 1999, J. Biol. Chem. 274, 6285-6294) of the proximal ZAP-70 kinase (p-ZAP-70; row 4), phospholipase-C-γ (p-PLC-γ; row 5), phosphorylated distal MAP kinases Erk1/2 (p42) and p38, and phosphorylated transcription factor STAT1 (p-STAT1, row 6). In notable contrast, expression of total ZAP-70 protein was significantly elevated in memory compared to naive CD4 T cells, manifested by a 5 fold increase in mean fluorescent intensity (FIG. 2A, row 3), with the augmented expression ranging from 3-5-fold in multiple experiments (n>10).

Figure 9:
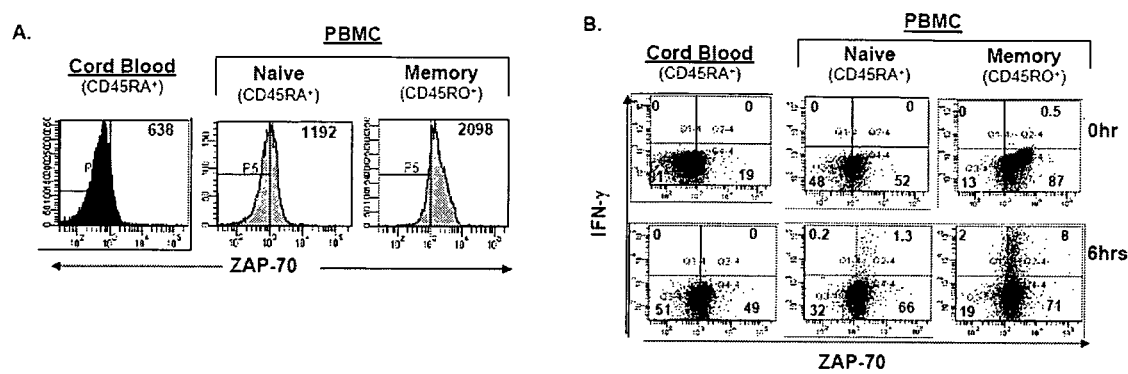
FIG. 9A, 9B: ZAP-70 expression and functional coupling in human CD4 T-cells. (A) Expression of ZAP-70 in human CD4 T-cells. Naive (CD45RA) CD4 T cells from cord blood and PBMC and memory (CD45RO) from PBMC were isolated and analyzed for intracellular ZAP-70 expression shown as histograms gated on CD4+CD45RA+ (naive) and CD4+CD45RO+ (memory) populations, with numbers indicating the mean fluorescence intensity, and markers drawn based on isotype controls. (B) Changes in IFN-γ production versus ZAP-70 levels in naive and memory CD4 T cells at resting (0 hr) and upon 6 hrs activation with anti-CD3/anti-CD28-coated Dynabeads™ (Dyanal Biotech). Naïve CD4 T-cells were gated on CD4+CD45RA+ while memory CD4 T-cells were gated on CD4+CD45RO+. The percentage of population in each quadrant is indicated by a number in the respective quadrant and the quadrant position was drawn based on isotype controls. Data shown here is representative of three independent experiments from three different donors.

We also analyzed ZAP-70 expression in human T cells subsets, and found that human peripheral blood CD45RO$^+$ memory CD4 T cells expressed the highest level of ZAP-70 protein that was twofold greater than ZAP-70 expression in CD45RA$^+$ phenotype adult CD4 T cells (that contain heterogeneous population of naive and non-naive T cells), and three-fold greater than pure naive CD4 T cells in cord blood (FIG. 9A). These results establish elevated ZAP-70 expression as a novel feature of antigen-specific and polyclonal mouse and human memory CD4 T cells, and validate the OVA-specific system for examining mechanisms for functional coupling and regulation of high ZAP-70 expression in memory CD4 T cells.

Increased ZAP-70 expression in memory versus naive CD4 T cells occurs in the context of comparable surface expression of CD4 and CD3ε (FIG. 2B), with 84% of memory CD4 T cells exhibiting a CD3ε$^+$/ZAP-70hi phenotype, compared to only 30% of naive CD4 T cells (FIG. 2B, row 2). Confocal microscopy to examine the expression, cellular localization, and TCR/CD3ε association of native ZAP-70 in situ in resting naive and memory CD4 T cells, likewise reveals elevated expression of the ZAP-70 kinase in memory compared to naive CD4 T cells, with comparable CD3ε levels. ZAP-70 expression in memory CD4 T cells is concentrated around the plasma membrane, with areas of CD3ε and ZAP-70 co-localization apparent in resting memory CD4 T cells and not present in resting naive T cells. These results demonstrate a marked increase in ZAP-70 expression in situ and constitutive association of ZAP-70 to CD3ε in resting memory versus naive CD4 T cells.

Similar to our findings with OVA-specific subsets, we also found higher expression of intracellular ZAP-70 protein in polyclonal BALB/c mouse memory (CD44hi) compared to naive (CD44lo) CD4 T cells and this quantitative increase in ZAP-70 expression ranged from 1.5-2.6-fold in polyclonal populations analyzed from multiple unmanipulated mice (FIG. 2C). These results establish elevated ZAP-70 expression as a novel feature of antigen-specific and polyclonal mouse memory CD4 T cells, and validates the OVA-specific system for examining mechanisms for functional coupling and regulation of high ZAP-70 expression in memory CD4 T cells.

Figure 3:
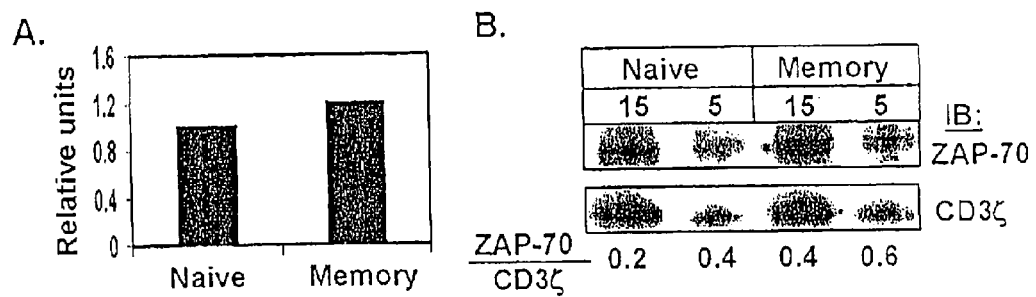
FIG. 3A, 3B. Regulation of ZAP-70 expression in resting CD4 T cells. (A) Real-time PCR analysis of ZAP-70 transcript expression in OVA-specific naive and memory CD4 T cells purified to >95% by Thy1$^+$ sorting expressed as a ratio of ZAP-70:CD4 transcripts. (B) Western blot analysis of ZAP-70 and CD3ζ protein expression in OVA-specific naive and memory CD4 T cells, in different dilutions of cell lysates. The densitometric ratio of ZAP-70: CD3ε expression in naive and memory subsets is indicated at the bottom.

In contrast to the difference in ZAP-70 protein expression, we found comparable transcript expression of ZAP-70 in naive and memory CD4 T cells by real-time PCR analysis (FIG. 3A), indicating that increased ZAP-70 protein expression in memory CD4 T cells is controlled post-transcriptionally. We also used western blot analysis to analyze ZAP-70 protein levels in titrated quantities of naive and memory CD4 T cell lysates, and found a relative increase in total denatured ZAP-70 protein levels in memory CD4 T cells (FIG. 3B), albeit of lower magnitude than that measured by intracellular staining of the native marker by flow cytometry, confirming the increased sensitivity of this single cell approach for assessing signaling distinctions in primary cells as suggested by Nolan and colleagues (Sachs et al., 2005, Science 308, 523-529).

Example 3

Figure 4:
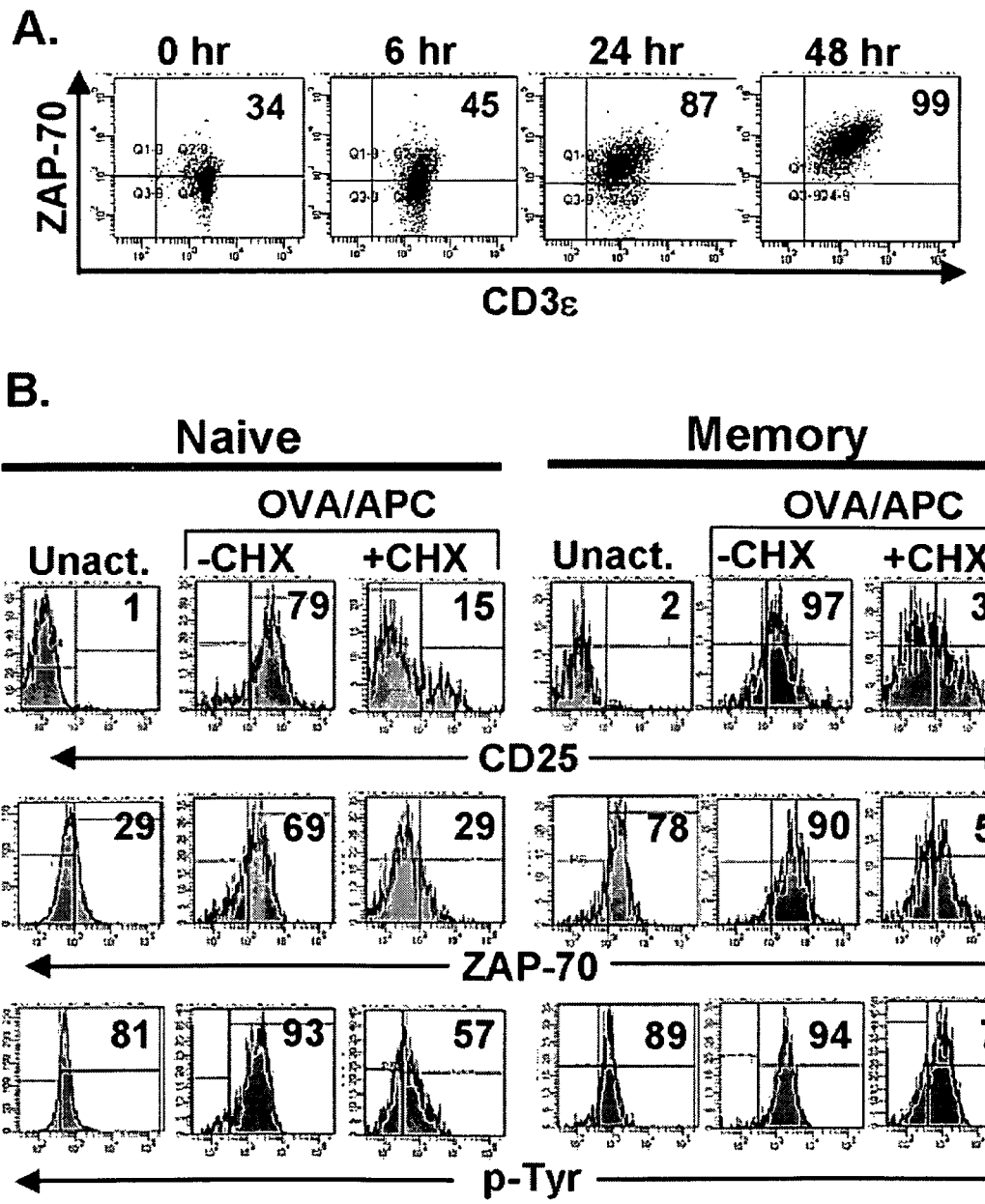
FIG. 4A, 4B. Regulation of ZAP-70 expression in antigen-stimulated naive and memory CD4 T cells. (A) Changes in expression of ZAP-70$^+$CD3ε$^+$ in OVA-specific naive CD4 T cells in the resting state and following stimulation with OVA/APC for 6-48 hrs. Plots are gated on live KJ1-26$^+$ cells, with quadrants drawn based on isotype controls and the number in the right-most quadrant indicates percentage of ZAP-70$^+$CD3ε$^+$ cells. Results are representative of three independent experiments. (B) Elevated ZAP-70 expression during activation requires protein synthesis in naive, but not in memory CD4 T cells. Histograms show surface CD25 expression and intracellular ZAP-70 expression and total tyrosine phosphorylation (p-Tyr) in naive and memory CD4 T cells activated for 24 hrs with OVA/APC in the presence of cycloheximide or vehicle control. Numbers indicate percentage positive, based on isotype controls (indicated by markers) for each parameter. Viability after 24 hrs in cycloheximide averaged 70%. Results are representative of three independent experiments.

Regulation of ZAP-70 Protein Expression Following Antigen Activation of Naive and Memory CD4 T Cells Our results showing high ZAP-70 expression in previously primed memory T cells suggested that antigenic priming of naive CD4 T cells might also lead to increased ZAP-70 expression. We thus stimulated OVA-specific naive CD4 T cells with OVA/APC for time points of 6-48 hrs, and assessed ZAP-70 expression in conjunction with activation phenotype and functional parameters. Stimulation of naive T cells with OVA/APC for 6 hours led to slight increases in expression of CD69, an early activation marker (Paolini et al., 2001, Proc. Natl. Acad. Sci. USA 98, 9611-9616; Herndon et al., 2001, J. Immunol. 166, 5654-5664; Wange et al., 1995, J. Biol. Chem. 270, 944-948) and no significant increases in CD25 or ZAP-70 expression (FIG. 4A). By contrast, after 24-48 hrs of stimulation with OVA/APC there was extensive upregulation of CD25 and CD69 as previously described (Moulton et al., 2006, supra), and substantial increases in the level of ZAP-70 protein expression with all cells exhibiting a CD3ε+/ZAP-70hi phenotype (similar to memory T cells) after 48 hrs of activation (FIG. 4A). Confocal analysis likewise demonstrates in situ increases in ZAP-70 expression on antigen-stimulated naive CD4 T cells after 24-48 hrs accompanied by increased co-localization of CD3c and ZAP-70 similar to resting memory CD4 T cells, and enhanced clustering of ZAP-70hi/CD3ε+ cells.

Because naive CD4 T cells require sustained activation to attain levels of ZAP-70 comparable to resting memory CD4 T cells, we hypothesized that ZAP-70 protein synthesis may be differentially regulated in these two subsets. We used the protein synthesis inhibitor cycloheximide (CHX) to examine how ZAP-70 expression, activation and signaling are regulated in antigen-stimulated naive and memory CD4 T cells. Treatment of naive and memory CD4 T cells +/−antigen for 6 hrs with cycloheximide did not affect the resting state level of ZAP-70 or intracellular tyrosine phosphorylation while 24 hrs treatment showed differential effects on the two subsets. For naive T cells, antigenic stimulation for 24 hrs led to significant up-regulation of CD25 and ZAP-70 expression that was completely inhibited in the presence of CHX (FIG. 4B, compare column 2 and 3), indicating that de novo protein synthesis is required for ZAP-70 up-regulation. Antigen stimulation of memory CD4 T cells also resulted in CD25 up-regulation, and slight increases in the already high level of ZAP-70 expression (FIG. 4B, column 5). While CHX treatment inhibited CD25 up-regulation on antigen-stimulated memory CD4 T cells, the high level of ZAP-70 expression was maintained on >50% of memory CD4 T cells (FIG. 4B, last column). In addition, CHX treatment also significantly inhibited increases in total intracellular p-Tyr levels observed in activated naive CD4 T cells, but did not affect p-Tyr levels in memory T cells (FIG. 4B, last row). These results indicate that maintenance of elevated ZAP-70 expression and basal tyrosine phosphorylation in memory CD4 T cells is only partially dependent on protein synthesis.

Example 4

Coupling of Elevated ZAP-70 Expression to Effector Function

Figure 5:
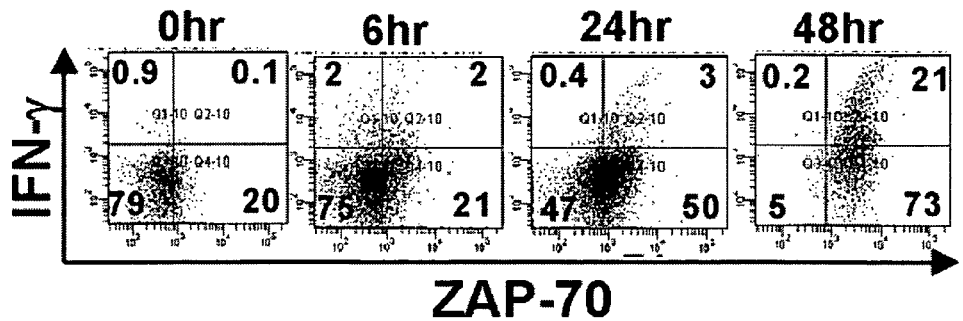
FIG. 5A, 5B: Elevated ZAP-70 expression correlates with the acquisition of effector function. (A) Intracellular ZAP-70 versus IFN-γ production in resting (0 hr) and after different periods of stimulation with OVA/APC of naive (6, 24, 48 hr) and memory (6, 24 hr) CD4 T cells. Results are gated on CD4$^+$KJ1-26$^+$ cells, and number in each quadrant indicates the percentage of the respective population. Results are representative of three independent experiments. (B) Correlation of ZAP-70hi expression with IFN-γ production, collated from three independent experiments.
Figure 5:
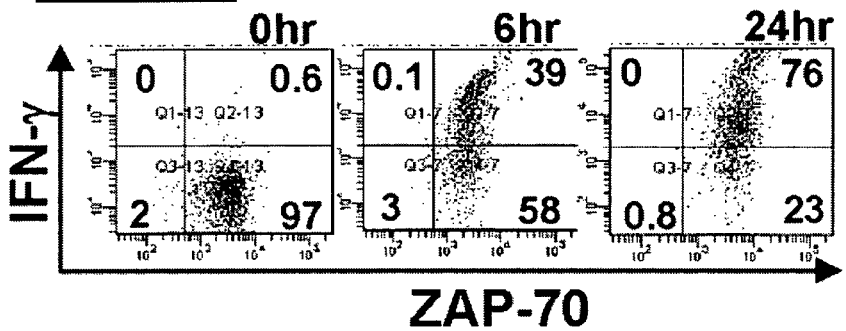
Figure 5:
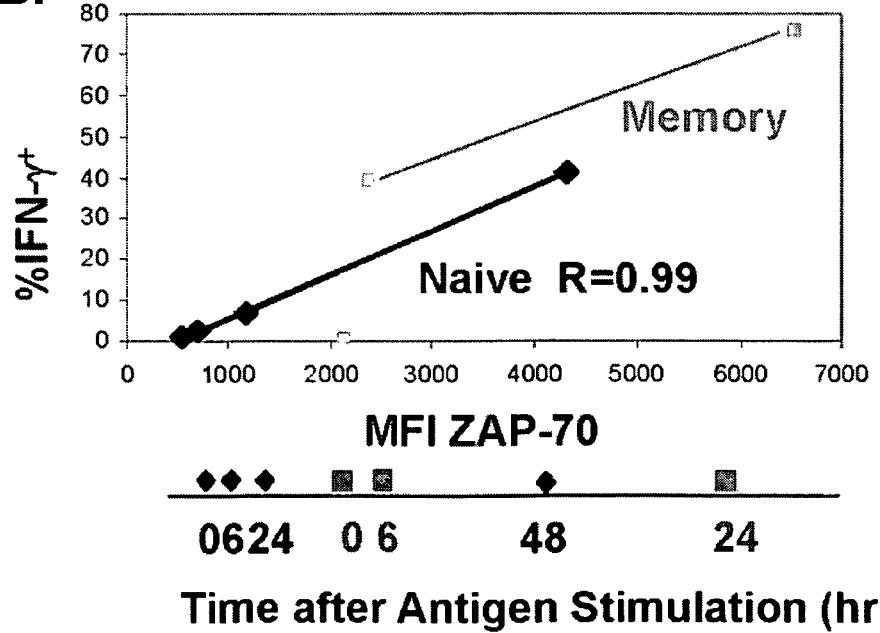

We asked whether elevated ZAP-70 expression coupled to effector function by simultaneous analysis of ZAP-70 expression and IFN-γ production in antigen-stimulated naive and memory CD4 T cells. Activation of naive CD4 T cells with OVA/APC for 6-48 hrs resulted in acquisition of IFN-γ production exclusively from the ZAP-70hi population (FIG. 5A), with increased IFN-γ production from ZAP-70hi compared to ZAP-70lo cells most apparent after 24 hrs of antigen stimulation. Analysis of the level of ZAP-70 versus IFN-γ production from resting and antigen-stimulated naive CD4 T cells reveals a strong correlation between increased ZAP-70 expression and increased effector function (R=0.99, FIG. 5B). For memory CD4 T cells the constitutive ZAP-70hi population produces IFN-γ rapidly, and ZAP-70 expression is further increased after 24 hrs with almost all memory CD4 T cells producing IFN-γ (FIG. 5A, B). Similar results showing IFN-γ production exclusively from ZAP-70hi cells were obtained following short-term stimulation of human T cells (FIG. 9B).

Figure 6:
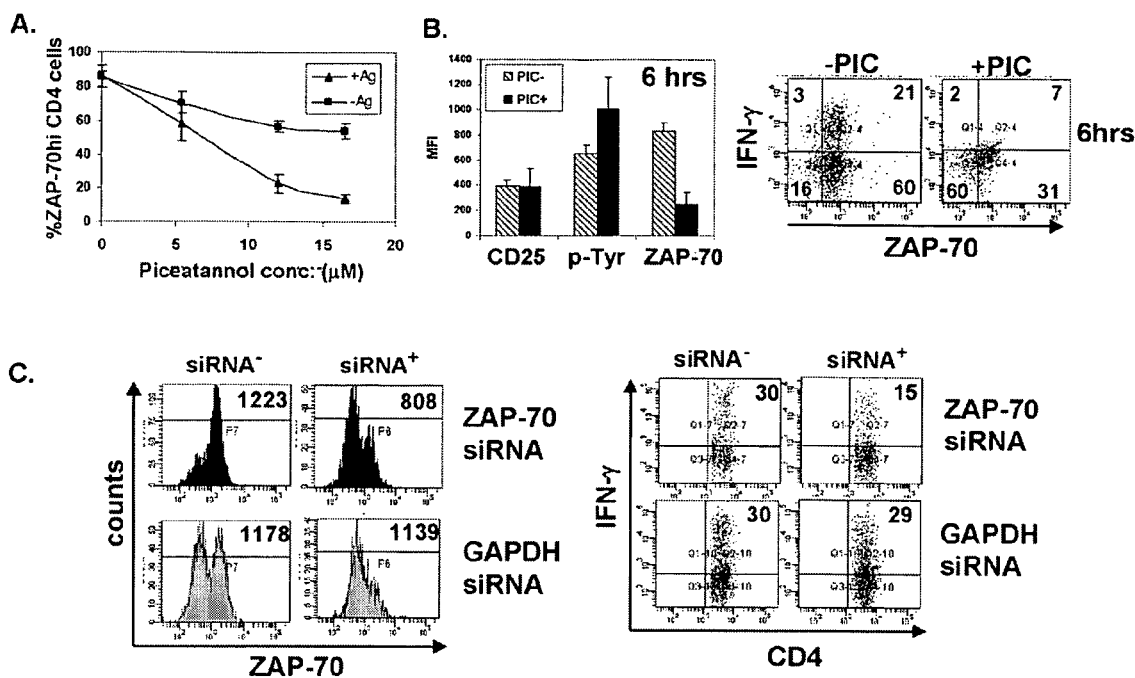
FIG. 6A, 6B, 6C: Downmodulation of ZAP-70 expression in memory CD4 T cells inhibits recall IFN-γ production. (A) Dose response curve of piceatannol and its effect on the level of ZAP-70 expression in memory CD4 T cells cultured +/−OVA/APC for six hrs. Memory CD4 T cells used here were isolated from RAG2$^{-/-}$ adoptive hosts >2 months post-transfer of DO11.10 CD4 T cells primed for three days. (B) Left: Histograms show expression of CD25, p-Tyr and ZAP-70 in OVA-specific memory CD4 T cells activated with OVA/APC for 6 hrs, all gated on CD4$^+$KJ1-26$^+$, and expressed as MFI of each marker. Right: ZAP-70$^+$/IFN-γ$^+$ production in control (−PIC) and piceatannol-treated memory (+PIC) CD4 T cells following 6 hrs of activation. Quadrants were drawn based on isotype control and the number in each quadrant represents the percentage of the respective population. Data shown in (A) and (B) are from three independent experiments. (C) siRNA-mediated knockdown of ZAP-70. OVA-specific memory CD4 T cells were transfected with ZAP-70 specific Cy3-labeled siRNA (5 μM) or Cy3-labeled control GAPDH siRNA (see methods). Transfected CD4 T cells were activated with APC and OVA-peptide for 24 hrs and intracellular ZAP-70 staining and IFN-γ production was measured by ICS. Left: Total intracellular ZAP-70 expression of silenced (siRNA$^+$; gated on Cy3$^+$ cells) and unsilenced (siRNA$^-$; gated on Cy3-negative cells) in ZAP-70 and control GAPDH siRNA-transfected cells, with MFI indicated in each plot. Right: IFN-γ production from silenced (siRNA$^+$) and unsilenced (siRNA$^-$) populations in ZAP-70- and GAPDH-siRNA transfected cells. Results are representative of two independent experiments.

To determine a mechanistic link between ZAP-70 expression and rapid effector capacity, we took two approaches to reduce ZAP-70 protein expression in memory T cells and examine functional outcome. For the first approach, we used the Syk/ZAP-70 tyrosine kinase inhibitor piceatannol (Soede et al., 1998, J. Cell Biol. 142, 1371-1379) that we found reduced ZAP-70 expression in a dose-dependent fashion in antigen-stimulated memory CD4 T cells (FIG. 6A). When memory CD4 T cells were stimulated with OVA/APC in the presence of piceatannol for 6 hrs, ZAP-70 expression was specifically reduced without affecting the basal level of CD25 and total p-Tyr content (FIG. 6B, left), and resulted in a striking inhibition of rapid IFN-γ production (FIG. 6B, right). As a second approach, we used RNA silencing (siRNA) (Hannon, G. J., 2002, Nature 418, 244-251) to drive down expression of ZAP-70 in memory CD4 T cells ex vivo and determine effects on IFN-γ production. We transfected fluorescently-coupled siRNAs specific for ZAP-70 or GAPDH into resting memory T cells using nucleofection (see methods) that we previously found enabled transfection of resting memory T cells (Lai et al., 2003, J. Immunol. Methods 282, 93-102). Specific silencing of ZAP-70 led to a reduction in ZAP-70 expression indicated by a reduction in the MFI of ZAP-70 in silenced (siRNA$^+$) compared to unsilenced (siRNA$^-$) populations, and ZAP-70 expression in siRNA$^+$ and siRNA$^-$ control GAPDH transfectants. This siRNA-mediated reduction in ZAP-70 expression resulted in a 50% reduction in the proportion of memory T cells producing IFN-γ, compared to the higher fraction of IFN-γ producers in siRNA$^-$ and GAPDH siRNA memory T cell transfectants (FIG. 6C, right). These results demonstrate that ZAP-70 signaling is essential for both early and late effector function from antigen-recalled memory CD4 T cells, and that a selective reduction of ZAP-70 expression in memory T cells inhibits their rapid recall.

Example 5

Figure 7:
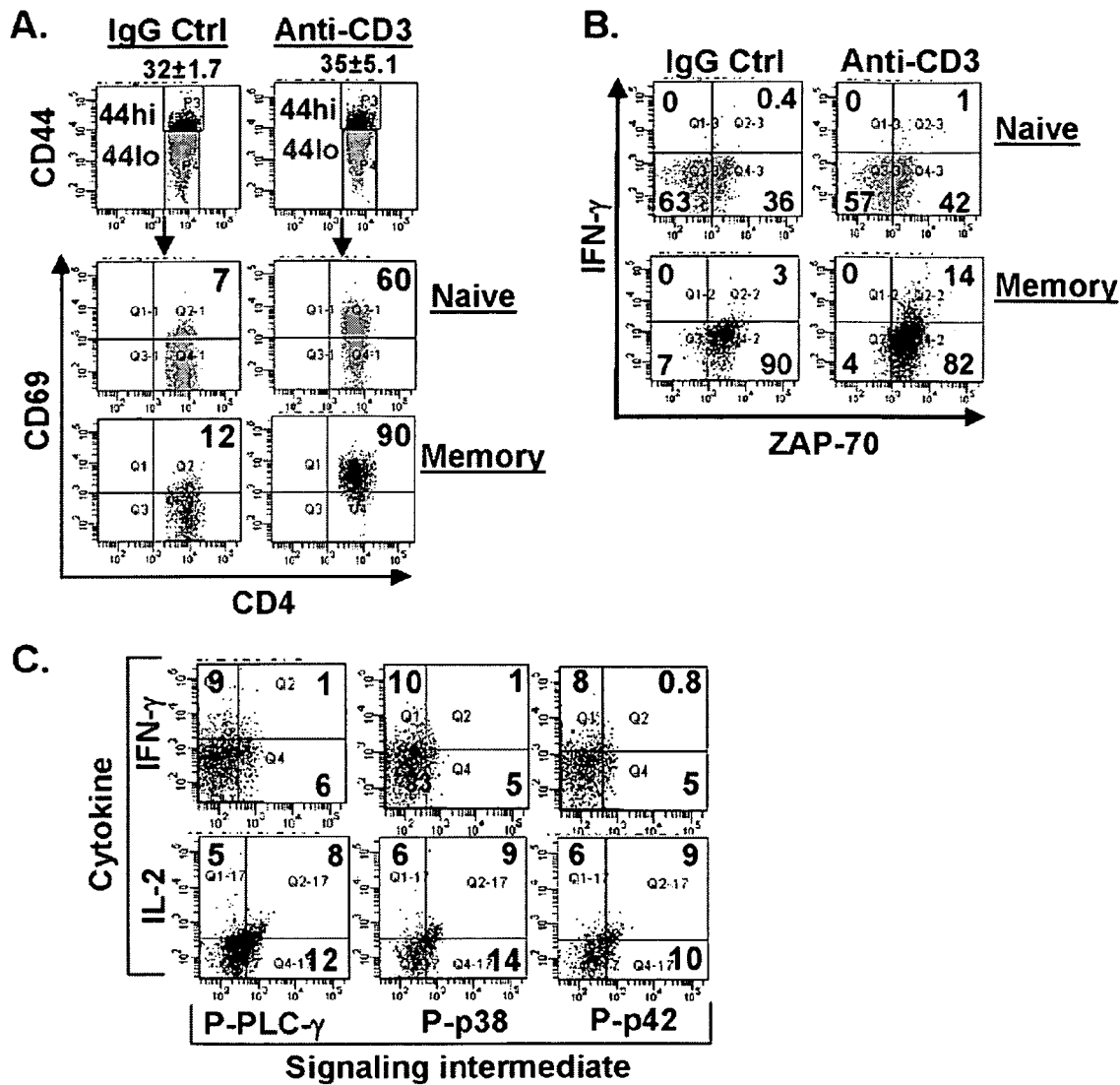
FIG. 7A, 7B, 7C: In vivo analysis of signaling and function from polyclonal naive and memory CD4 T cells. (A) Mice (n=3 per group) were injected with anti-CD3 or control IgG and spleens were harvested after 4 hours. First row: CD44 expression of CD4 T cells in anti-CD3 versus control-treated mice showing delineation and gate for memory (CD44hi) and naive (CD44lo) T cells. The proportion of CD44hi CD4 T cells in control IgG versus anti-CD3 treated mice is indicated as 32±1.7 and 35±5.1 from 3 mice per group. Rows 2 and 3: CD69 expression on naive and memory CD4 T cells in anti-CD3 versus control treated mice, with the number in the upper quadrant indicating percentage of CD69hi cells. (B) Functional coupling of ZAP-70 versus IFN-γ production gated on naive (CD44lo) and memory (CD44hi) CD4 T cells in IgG versus anti-CD3-treated mice. Quadrants were drawn based on isotype control and the number in each quadrant represents the percentage of the respective population. Results are representative of three independent experiments. (C) Correlation of downstream signaling and cytokine production in anti-CD3 stimulated memory CD4 T cells in vivo. Expression of phospho-p38 and phospho-p42 MAP kinases and phospho-PLC-γ versus IL-2 or IFN-γ production in memory CD4 T cells isolated from anti-CD3 treated mice. No IFN-γ or IL-2 was observed in cells from control-treated mice and quadrants are drawn based on isotype controls.

In Vivo Coupling of TCR-Mediated Signaling and Function in Naive and Memory CD4 T Cells While our results establish differential coupling of function to signaling in memory CD4 T cells stimulated ex vivo, we asked whether similar functional coupling of signaling occurred in vivo in polyclonal memory CD4 T cells. To establish a system for analysis of in vivo signaling and function, we administered low dose anti-CD3 antibody to unmanipulated BALB/c mice that is known to promote rapid TCR/CD3-triggered in vivo responses (Scott et al., 1990, J. Immunol. 145, 2183-2188), and recovered splenocytes after 4 hours from anti-CD3 and control Ig-treated mice. The percentages of memory (CD44hi) and naive (CD44lo) phenotype CD4 T cells were comparable in mice injected either with anti-CD3 or control IgG (FIG. 7A, top), indicating that the short-term treatment did not alter the overall proportion of these subsets. Both naive and memory CD4 T cells exhibited upregulation of the early activation marker CD69 following anti-CD3 stimulation, with a higher proportion of memory CD4 T cells being CD69hi (FIG. 7A), indicating that in vivo anti-CD3 treatment triggered TCR signaling in both subsets. Analysis of ZAP-70 and IFN-γ production from naive and memory CD4 T cells in vivo revealed that CD44hi memory T cells exhibiting a high level of ZAP-70 expression mediated rapid IFN-γ production in response to anti-CD3 in vivo (but not control IgG), whereas naive CD4 T cells expressing a lower level of ZAP-70 did not secrete IFN-γ (FIG. 7B), similar to our ex vivo stimulation results. These results establish that rapid effector function occurs exclusively from ZAP-70hi cells in vivo. We hypothesized that the coordinate analysis of signaling events and cytokine production as performed with ZAP-70 and IFN-γ could be informative for assessing correlations between downstream signaling events and function. To test this approach, we analyzed the phosphorylation of downstream mediators including PLC-γ, p38 MAP kinase and the p42 erk kinase in conjunction with IFN-γ and IL-2 production from in vivo anti-CD3 stimulated memory CD4 T cells as above (in vivo activated naive CD4 T cells did not produce measurable IFN-γ or IL-2 after 4 hours). We found that while a small proportion of memory CD4 T cells exhibited phosphorylated PLC-γ, -p38 and -p42 after short-term anti-CD3 stimulation (FIG. 7C), the majority of rapid IFN-γ production occurred from memory cells that did not exhibit these downstream phosphorylations (FIG. 7C, top row). By contrast, IL-2 production from memory CD4 T cells was preferentially observed from the subset that upregulated phosphorylated PLC-γ, p38 and p42 (FIG. 7C, bottom row), consistent with their known signaling requirement for IL-2 production in primary T cells and T cell lines (Kane et al., 2000, Curr. Opin. Immunol. 12, 242-249; Yablonski et al., 2001, Mol. Cell. Biol. 21, 4208-4218). These results suggest that simultaneous assessment of phosphorylation events and function, while measured at later timepoints compared to conventional biochemical analyses, may be useful for revealing important associations between signaling events and functional output.

Example 6

Quantitative Differences in Distal Signaling Mark Early and Late IFN-γ Production We next applied the analysis of downstream signaling and function to determine whether increased ZAP-70 expression and rapid IFN-γ production in memory T cells was associated with alterations in downstream signaling. We activated OVA-specific naive and memory CD4 T cells with antigen over a broad kinetic window and examined the expression of phosphorylated distal signaling intermediates (p-PLC-γ, phospho-p42 and -p38 MAP kinases and p-STAT1) in conjunction with ZAP-70 protein expression and IFN-γ production. We found qualitative and kinetic differences in signaling profiles linked to IFN-γ production in naive and memory CD4 T cells. A representative analysis of ZAP-70, PLC-γ1 and IFN-γ demonstrates an accumulation of downstream PLC-γ1 phosphorylation following similar kinetics in naive and memory CD4 T cells, with 24 hrs of antigen stimulation resulting in a majority of p-PLC-γ1$^+$ cells (data not shown). Importantly, ZAP-70 expression and phosphorylated-PLC-γ1 delineate three distinct signaling profiles in naive and memory subsets: (1) ZAP-70$^{lo}$/p-PLC-γ1$^{lo}$ as in resting and 6-hr stimulated naive CD4 T cells, (2) ZAP-70$^{hi}$/p-PLC-γ$^{lo}$, as in resting and 6 hr-stimulated memory CD4 T cells, and (3) ZAP-70$^{hi}$/p-PLC-γ$^{hi}$ found naive and memory CD4 T cells stimulated for 24 hrs (data not shown). For naive T cells, the IFN-γ-producing population emerging after 24-48 hrs derives exclusively from the ZAP-70$^{hi}$/p-PLC-γ$^{hi}$ subset (data not shown). By contrast, IFN-γ-producing memory CD4 T cells bore two distinct signaling profiles at early and late times of antigen stimulation; after 6 hrs stimulation the IFN-γ$^+$ population derived predominantly from the ZAP-70$^{hi}$/p-PLC-γ$^{lo}$ subset (data not shown), as also observed in vivo, whereas after 24 hrs of stimulation IFN-γ producers derived from the ZAP-70$^{hi}$/p-PLC-γ$^{hi}$ subset (data not shown).

Similar to our results with p-PLC-γ, we found an accumulation of distal phosphorylated MAP kinases (p38 and p42) and STAT1 at late times after activation (≧24 hrs for naive and memory cells), also consistent with previous biochemical results showing increased phosphorylation after sustained T cell activation (Hussain et al., 2002, supra; Ahmadzadeh et al., 1999, J. Immunol. 163, 3053-3063; Krishan et al., 2001, Blood 97, 3851-3859), with negligible accumulation after 6 hrs of stimulation in either naive or memory CD4 T cells. IFN-γ production from activated naive CD4 T cells occurred exclusively from cells with phosphorylated distal intermediates (data not shown) together with increased ZAP-70. By contrast, early IFN-γ production from antigen-stimulated memory CD4 T cells derived from ZAP-70hi cells lacking p-p38, p-p42 or pSTAT1 (data not shown), whereas late IFN-γ production from memory CD4 T cells occurred from cells that had accumulated phosphorylated intermediates, similar to naive cells (data not shown). When taken together, these results demonstrate that rapid IFN-γ by memory CD4 T cells occurs from cells that do not exhibit sustained increases in downstream phosphorylation events, contrasting the extensive accumulation of phosphorylation accompanying late IFN-γ production from stimulation of naive or memory CD4 T cells.

Example 7

Differential Correlation of Naïve CD4 T Cells to ZAP-70 for Production of TNFα and IFNγ

Table 2 shows TNFα and IFN-γ production from resting and antigen-stimulated naive CD4 T cells. OVA-specific naive CD4 T cells were activated with OVA peptide and splenic APC for different time periods (6-48 hrs). Cytokine production (TNFα and IFN-γ) was assessed by intracellular staining. Changes in mean fluorescence intensity (MFI) of ZAP-70 over a period of antigen activation leading to the changes in TNFα and IFN-γ levels are shown. Change in the relative value of mean fluorescence demonstrates that there is differential correlation to ZAP-70 for TNF-α and IFN-γ production.

TABLE 2

| Time of CD4 T cell activation (hr) | ZAP-70 (MFI) | TNFα Production (%) | IFNγ Production (%) |
|---|---|---|---|
| 0 | 540 | 0.3 | 0.1 |
| 6 | 705 | 6.8 | 0.7 |
| 24 | 1166 | 38.6 | 9 |
| 48 | 4325 | 86.8 | 19.6 |

Discussion

The rapid recall response elicited by memory T cells is a hallmark of immunological memory; however the underlying mechanism(s) for this efficacious response not been revealed. In this study, we present a novel analysis of TCR-coupled signaling and function in resting and antigen-stimulated naive and memory CD4 T cells, and reveal distinct signaling pathways linked to effector function in these subsets. Specifically, we identify a striking elevation in expression of the ZAP-70 protein tyrosine kinase in antigen specific and polyclonal memory compared to naive CD4 T cells. High level ZAP-70 expression in memory CD4 T cells was maintained independent of protein synthesis, and was required for their rapid recall function. In vitro results with our antigen specific system (FIG. 8) together with in vivo analysis of polyclonal naive and memory CD4 T-cells (FIG. 7) indicate that rapid IFN-γ from memory CD4 T cells occurs from ZAP-70hi cells in the context of fewer downstream signaling events compared to IFN-γ production resulting from sustained activation of naive CD4 T cells. Together, our results reveal a unique biochemical signature of memory CD4 T cells suggesting that increased ZAP-70 and its association with the TCR/CD3 complex may initiate more efficient signaling from TCR ligation to enhanced effector function.

We demonstrate here elevated expression of the ZAP-70 protein in both antigen specific and polyclonal mouse memory CD4 T cells as an inherent property of T cell memory. The greatest difference in ZAP-70 expression (>5 fold) occurred between pure naive DO11.10 TCR cells and memory CD4 T-cells in the mouse. Polyclonal naive (CD44lo) T cells in adult mice showed levels of ZAP-70 slightly greater than the pure naive populations, suggesting that levels of ZAP-70 may also be affected by homeostatic turnover of these cells in the periphery (Song et al., 2005, Proc. Natl. Acad. Sci. USA 102, 7916-7921) or during aging (Miller, R. A., 2000, Vaccine 18, 1654-1660). The comparable transcript level of ZAP-70 in resting naive and memory CD4 T cells coupled with our findings that elevated ZAP-70 expression in memory CD4 T cells can be maintained independent of new protein synthesis together indicate increased stability and/or reduced turnover of the ZAP-70 protein in memory T cells. ZAP-70 protein stability in NK cells and lymphomas has been linked to both ubiquitin-mediated regulation and association to molecular chaperones (Castro et al., 2005, Blood 106, 2506-2512; Paolini et al., 2001, Proc. Natl. Acad. Sci. USA 98, 9611-9616), and these mechanisms could also be operable in T cells. The increased stability of specific proteins in memory CD4 T cells may reflect an overall change in cell physiology that contribute to their enhanced functions, lifespan, and turnover.

Our results demonstrate that elevated ZAP-70 expression can act as a biochemical indicator for effector capacity, as IFN-γ-production was exclusively from T cells that had up-regulated ZAP-70 expression in CD4 T-cells. Moreover, we show that elevated ZAP-70 expression is required for rapid IFN-γ from memory CD4 T cells, as early IFN-γ production was inhibited when ZAP-70 expression was selectively downmodulated using siRNA, and completely blocked when ZAP-70 expression and signaling was prevented by the inhibitor piceatannol. Although ZAP-70 signaling has been linked to downstream processes such as PLC-γ activation and calcium flux that lead to IL-2 production (Herndon et al., 2001, J. Immunol. 166, 5654-5664; Wange et al., 1995, J. Biol. Chem. 270, 944-948), our findings indicate that ZAP-70 is a critical proximal transducer for effector function and a key regulator of recall function in memory CD4 T cells.

The increased protein expression of ZAP-70 appeared to be more central in regulation of memory T cell function, and we found only modest upregulation of ZAP-70 phosphorylation at residue Y319 (shown to be important in TCR signaling (Di Bartolo et al., 1999, J. Biol. Chem. 274, 6285-6294) in memory T cells at earlier time points (30 min-6 hrs) that did not correlate with function. These findings are consistent with our previous results of low phospho-ZAP-70 content in lysates of phenotypic memory CD4 T cells (Farber et al., 1997, Eur. J. Immunol. 27, 2094-2101); however, we cannot rule out transient phosphorylation events (Yokosuka et al., 2005, Nat. Immunol. 6, 1253-1262), or other regulatory phosphorylation sites playing a role (Zhao et al., 1999, Mol. Cell. Biol. 19, 948-956). Our finding of increased ZAP-70 associated to the TCR/CD3 complex also suggests that signaling efficiency may likewise be controlled via these increased proximal associations as previously suggested (Duplay et al., 1994, J. Exp. Med. 179, 1163-1172; Thome et al., 1995, J. Exp. Med. 181, 1997-2006).

Figure 8:
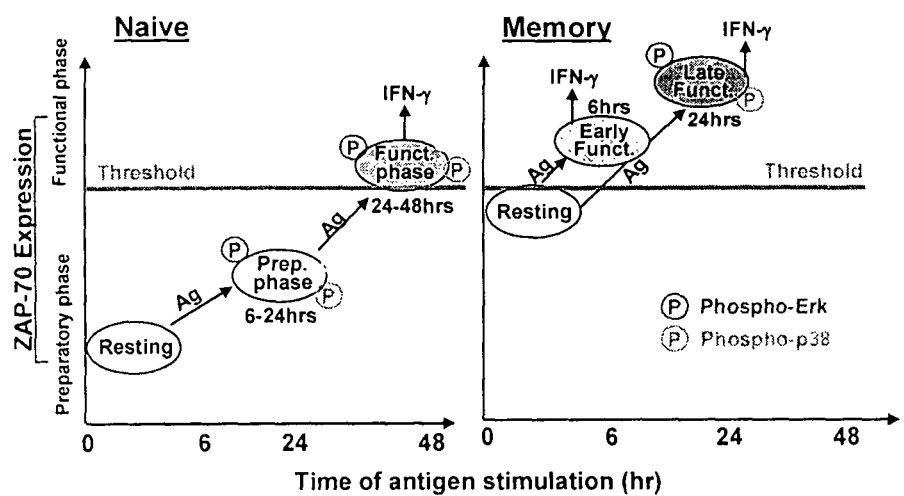
FIG. 8: Model for differential coupling of signaling to effector function in memory versus naive CD4 T cells. Naive and memory CD4 T cells are depicted as a function of ZAP-70 expression (y axis for both plots) versus the time of antigen stimulation (x-axis). For naive T cells, antigen activation leads first to a "preparatory phase" characterized by increased ZAP-70 expression and downstream phosphorylation, followed by a "functional phase" marked by elevated ZAP-70 expression, and phosphorylation. Resting memory CD4 T cells exhibit elevated ZAP-70 expression and rapidly progress to and early functional phase ("Early Funct."), with sustained activation leading to a late functional phase ("Late funct.") with a signaling profile similar to that of naive T cells.

The majority of studies of TCR-mediated signaling examine intracellular events seconds to minutes following TCR ligation. By contrast, we demonstrate that sustained activation of T cells leads to profound changes in the expression and phosphorylation state of TCR-coupled signaling intermediates, and these changes are differentially associated with distinct T cell functions. We propose a signaling threshold model in which the level of ZAP-70 controls effector responses in CD4 T cells, with increased ZAP-70 expression leading to more efficient cellular responses (FIG. 8). In naive CD4 T cells, ZAP-70 expression is low accounting for the lack of effector function; however, sustained antigenic stimulation (6-24 hrs) leads to increased ZAP-70 expression requiring new transcription and translation (FIG. 4B) and also an accumulation of downstream phosphorylation events comprising a preparatory phase with low functional output (FIG. 8). When the minimum threshold level of ZAP-70 expression is achieved, cells enter into a functional phase, leading to IFN-γ production. For memory CD4 T cells, the level of ZAP-70 in the resting state is already at this threshold level; hence the preparatory phase is bypassed and cells enter directly into the early functional phase without the requirement for continual downstream phosphorylation (FIG. 8). Sustained stimulation of memory CD4 T cells results in late effector function marked by further increases in ZAP-70 expression and the accumulation of phosphorylation events similar to the functional phase of naive T cells, and distinct from the early functional phase.

The involvement of ZAP-70 expression in setting up a threshold value for signaling has been recently demonstrated in chronic lymphocytic leukemia (CLL) (Chen et al., 2005, Blood 105, 2036-2041) in which ZAP-70 up-regulation has been associated with aggressive disease (Rassenti et al., N. Engl. J. Med. 351, 893-901). A certain threshold level of ZAP-70 expression in CLL cells was shown to enhance IgM signaling, and exceeding this threshold did not further enhance IgM signaling or downstream adaptor/signaling events (Chen et al., 2005, supra). These studies suggest that the ZAP-70 kinase may serve as a generalized proximal signaling threshold for downstream functions in lymphocytes. Additional downstream alterations in memory T cells such as epigenetic changes in cytokine loci (Northrop et al., 2006, J. Immunol. 177, 1062-1069) may synergize with the increased proximal signals to facilitate rapid recall responses.

In conclusion, our results provide: (1) novel biochemical insights into the rapid recall of memory T cells using a multiparameter approach, identifying elevated expression of the proximal ZAP-70 kinase and quantitative differences in downstream phosphorylation as critical elements that distinguish the memory pathway to efficacious responses; and (2) by altering the level of ZAP-70, one can modulate CD4 and/or CD8 T cells differentially to alter the levels of TNF-α and IFN-γ production.

All patents and publications mentioned and/or cited in this specification are indicative of the level of those skilled in the art to which the invention pertains. All patents and publications mentioned and/or cited herein are incorporated by reference to the same extent as if each individual publication was specifically and individually indicated as having been incorporated by reference in its entirety.

What is claimed is:

1. A method for differentiating a memory T cell with effector function from a memory T cell without effector function or a resting naïve T cell in a biological sample, said method comprising
   (i) isolating T cells from said sample; and
   (ii) measuring ZAP-70 protein expression in said isolated T cells and comparing amount of ZAP-70 protein expression in each cell to that in a control inactivated T cell, wherein an elevation in ZAP-70 protein expression relative to said inactivated T cell indicates a memory T cell with effector function.

2. The method of claim 1 wherein said method of measuring ZAP-70 is flow cytometry.

3. The method of claim 1 wherein said T cell is a CD4 or CD8 T cell.

* * * * *

UNITED STATES PATENT AND TRADEMARK OFFICE
CERTIFICATE OF CORRECTION

PATENT NO.        : 8,450,053 B2
APPLICATION NO.   : 12/733636
DATED             : May 28, 2013
INVENTOR(S)       : Meena Chandok, Donna Farber and Francesca Okoye It is certified that error appears in the above-identified patent and that said Letters Patent is hereby corrected as shown below:

In the Specifications

Please delete the language in lines 9 through 11 in Column 1, and replace it with the following language --This invention was made with government support under Grant Number AI042092 awarded by the National Institutes of Health. The government has certain rights in the invention.--

Signed and Sealed this
Thirtieth Day of July, 2013

Teresa Stanek Rea
*Acting Director of the United States Patent and Trademark Office*

SEQUENCE LISTING

```
<160> NUMBER OF SEQ ID NOS: 11

<210> SEQ ID NO 1
<211> LENGTH: 17
<212> TYPE: PRT
<213> ORGANISM: Mus musculus
<220> FEATURE:

<400> SEQUENCE: 1

Ile Ser Gln Ala Val His Ala Ala His Ala
 1               5                  10

Glu Ile Asn Glu Ala Gly Arg
                15

<210> SEQ ID NO 2
<211> LENGTH: 22
<212> TYPE: DNA
<213> ORGANISM: Artificial sequence
<220> FEATURE:
<223> OTHER INFORMATION: GAPDH forward primer

<400> SEQUENCE: 2
agcctcgtcc cgtagacaaa at                                           22

<210> SEQ ID NO 3
<211> LENGTH: 21
<212> TYPE: DNA
<213> ORGANISM: Artificial sequence
<220> FEATURE:
<223> OTHER INFORMATION: GAPDH reverse primer

<400> SEQUENCE: 3
tggcaacaat ctccactttg c                                            21

<210> SEQ ID NO 4
<211> LENGTH: 23
<212> TYPE: DNA
<213> ORGANISM: Artificial sequence
<220> FEATURE:
<223> OTHER INFORMATION: HPRT forward primer

<400> SEQUENCE: 4
```

-continued gctgacctgc tggattacat taa                                     23

<210> SEQ ID NO 5
<211> LENGTH: 28
<212> TYPE: DNA
<213> ORGANISM: Artificial sequence
<220> FEATURE:
<223> OTHER INFORMATION: HPRT reverse primer

<400> SEQUENCE: 5
tgatcattac agtagctctt cagtctga                                28

<210> SEQ ID NO 6
<211> LENGTH: 23
<212> TYPE: DNA
<213> ORGANISM: Artificial sequence
<220> FEATURE:
<223> OTHER INFORMATION: ZAP-70 reverse primer

<400> SEQUENCE: 6
gtaaattagt ccatccgcct tca                                     23

<210> SEQ ID NO 7
<211> LENGTH: 21
<212> TYPE: DNA
<213> ORGANISM: Artificial sequence
<220> FEATURE:
<223> OTHER INFORMATION: ZAP-70 forward primer

<400> SEQUENCE: 7
ctctggcagc tggtggagta c                                       21

<210> SEQ ID NO 8
<211> LENGTH: 21
<212> TYPE: DNA
<213> ORGANISM: Artificial sequence
<220> FEATURE:
<223> OTHER INFORMATION: CD4 forward primer

<400> SEQUENCE: 8
actggttcgg catgacactc t                                       21

<210> SEQ ID NO 9
<211> LENGTH: 23
<212> TYPE: DNA
<213> ORGANISM: Artificial sequence
<220> FEATURE:
<223> OTHER INFORMATION: CD4 reverse primer

<400> SEQUENCE: 9
tgatagctgt gctctgaaaa ccc                                     23

<210> SEQ ID NO 10
<211> LENGTH: 21
<212> TYPE: DNA
<213> ORGANISM: Artificial sequence
<220> FEATURE:
<223> OTHER INFORMATION: ZAP-70-specific siRNA sense

<400> SEQUENCE: 10
ggcggaugga cuaauuuact t                                       21

```
<210> SEQ ID NO 11
<211> LENGTH: 21
<212> TYPE: DNA
<213> ORGANISM: Artificial sequence
<220> FEATURE:
<223> OTHER INFORMATION: ZAP-70-specific siRNA antisense

<400> SEQUENCE: 11
guaaauuagu ccauccgcct t                                              21
```